US010125173B2

(12) United States Patent
Ruprecht et al.

(10) Patent No.: US 10,125,173 B2
(45) Date of Patent: Nov. 13, 2018

(54) HIV-1 V3 MIMOTOPES CAPABLE OF INDUCING CROSS-CLADE NEUTRALIZING ANTIBODIES

(71) Applicant: Texas Biomedical Research Institute, San Antonio, TX (US)

(72) Inventors: Ruth M. Ruprecht, Boston, MA (US); Michael Humbert, Boston, MA (US)

(73) Assignee: Texas Biomedical Research Institute, San Antonio, TX (US)

( * ) Notice: Subject to any disclaimer, the term of this patent is extended or adjusted under 35 U.S.C. 154(b) by 0 days.

(21) Appl. No.: 15/094,860

(22) Filed: Apr. 8, 2016

(65) Prior Publication Data

US 2016/0333055 A1  Nov. 17, 2016

Related U.S. Application Data

(63) Continuation of application No. 13/914,252, filed on Jun. 10, 2013, now Pat. No. 9,334,310, which is a continuation of application No. 13/075,761, filed on Mar. 30, 2011, now abandoned, which is a continuation of application No. PCT/US2009/005734, filed on Oct. 21, 2009.

(60) Provisional application No. 61/197,957, filed on Oct. 30, 2008.

(51) Int. Cl.
| | |
|---|---|
| *A61K 39/00* | (2006.01) |
| *A61K 39/395* | (2006.01) |
| *C07K 16/00* | (2006.01) |
| *A61K 39/12* | (2006.01) |
| *C07K 14/005* | (2006.01) |
| *A61K 39/21* | (2006.01) |
| *C07K 16/10* | (2006.01) |
| *C07K 16/42* | (2006.01) |
| *C12N 7/00* | (2006.01) |
| *A61K 38/00* | (2006.01) |

(52) U.S. Cl.
CPC ............ *C07K 14/005* (2013.01); *A61K 39/12* (2013.01); *A61K 39/21* (2013.01); *C07K 16/1063* (2013.01); *C07K 16/4216* (2013.01); *C12N 7/00* (2013.01); *A61K 38/00* (2013.01); *A61K 39/00* (2013.01); *A61K 2039/5256* (2013.01); *A61K 2039/53* (2013.01); *A61K 2039/55566* (2013.01); *A61K 2039/575* (2013.01); *C07K 2317/21* (2013.01); *C07K 2317/24* (2013.01); *C07K 2317/34* (2013.01); *C07K 2317/55* (2013.01); *C07K 2317/76* (2013.01); *C07K 2318/10* (2013.01); *C07K 2319/00* (2013.01); *C12N 2740/15022* (2013.01); *C12N 2740/16122* (2013.01); *C12N 2740/16134* (2013.01); *C12N 2740/16171* (2013.01); *C12N 2795/00043* (2013.01)

(58) Field of Classification Search
CPC ................... A61K 39/12; A61K 39/21; A61K 2039/5256; C07K 14/005; C12N 2740/16134
See application file for complete search history.

(56) References Cited

U.S. PATENT DOCUMENTS

2007/0054262 A1* 3/2007 Baker ...................... C07K 7/06
435/5

* cited by examiner

*Primary Examiner* — Barry A Chestnut
(74) *Attorney, Agent, or Firm* — Bracewell LLP; Karthika Perumal

(57) ABSTRACT

The invention provides methods, compositions and kits for treating and or preventing an HIV infection. For example, HIV envelope-like polypeptides (wild-type HIV polypeptides and mimotopes) may be administered to an individual so as to induce a protective immune response to HIV. Alternatively, antibodies directed to the HIV envelope-like polypeptides may be administered to an individual to treat or prevent an HIV infection and/or one or more symptoms associated with the infection (e.g., AIDS).

16 Claims, 10 Drawing Sheets

Specification includes a Sequence Listing.

The following peptides resemble the V3 loop: (name, amino acid sequence)

| NAME | AMINO ACID SEQUENCE | SEQ ID NO: |
|---|---|---|
| T12.1 | TKWVHTGPGERH | 102 |
| T12.2 | TRPPPGWTAYVT | 103 |
| T12.3 | MHKPIRTGPAEV | 104 |
| T12.4 | MSPPKHIRLGPN | 105 |
| T12.5 | GLRPGRAQPFYA | 106 |
| T12.6 | MPRASPGSPHYT | 107 |
| T12.7 | GLRPGMAQPFYA (identical to T12.11) | 108 |
| T12.9 | HAKLIRTGPVAV | 109 |
| T12.10 | TSRWDDVRHSIT | 110 |

The following peptides resemble the C-terminal domain: (name, amino acid sequence)

| NAME | AMINO ACID SEQUENCE | SEQ ID NO: |
|---|---|---|
| T7.1 | KAIRIAP | 111 |
| T7.2 | KAIRVGP (identical to T7.3) | 112 |
| T7.4 | KPLRLGP | 113 |
| Tc.1 | IRLGPGQ (identical to Tc.2) | 114 |

HIV-1 V3 MIMOTOPES CAPABLE OF INDUCING CROSS-CLADE NEUTRALIZING

FIG. 2 shows the alignment of mimotopes selected with serum from monkey RKl-8 with the sequence of homologous Gp160$_{SHIV-1157ip}$. HIV envelope-like polypeptides are grouped according to their motifs (V3, gp120 C-terminus, gp41 immunodominant region (IDR), KLIC, and membrane proximal external region (MPER)) and aligned to gp160$_{SHIV-1157ip}$ (grey rows). Linear homologies are shaded grey. Mimotopes are considered linear if they exhibited more than 50% linear amino acid identity.

FIG. 3 illustrates an amino acid sequence for gp160 and highlights the following domains: signal peptide, V1, V2, V3, V4, V5, C-terminus, fusion peptide, N-terminal heptad repeat region, immunodominant region, C-terminal heptad repeat domain, MPER, membrane-spanning domains 1 and 2, MSD3 and intracellular region.

FIG. 4 illustrates the location of mimotope A12.2 on Gp120. [Schreiber A, et al. J Comput Chem 26: 879-887, 2005]. 3DEX analysis was used to find structural homology between A12.2 (yellow, orange and green) and the surface of gp120 (PDB ID: 2B4C) with the CD4 binding site shown in red and CCR5 coreceptor contact sites in blue. The inset table shows partial V3 sequences for SHIV-1157ip, the protein structure used for the 3DEX analysis (2B4C), and A12.2. Amino acid residues resembling the parental sequence but too few to form a linear epitope are shown in yellow and orange. Residues identified by 3DEX as showing 3D homology are shown in green.

FIG. 5 illustrates the conformational dependence of mimotope A12.2 by dot spot analysis with phage affinity-purified serum antibodies.

Figure 8:
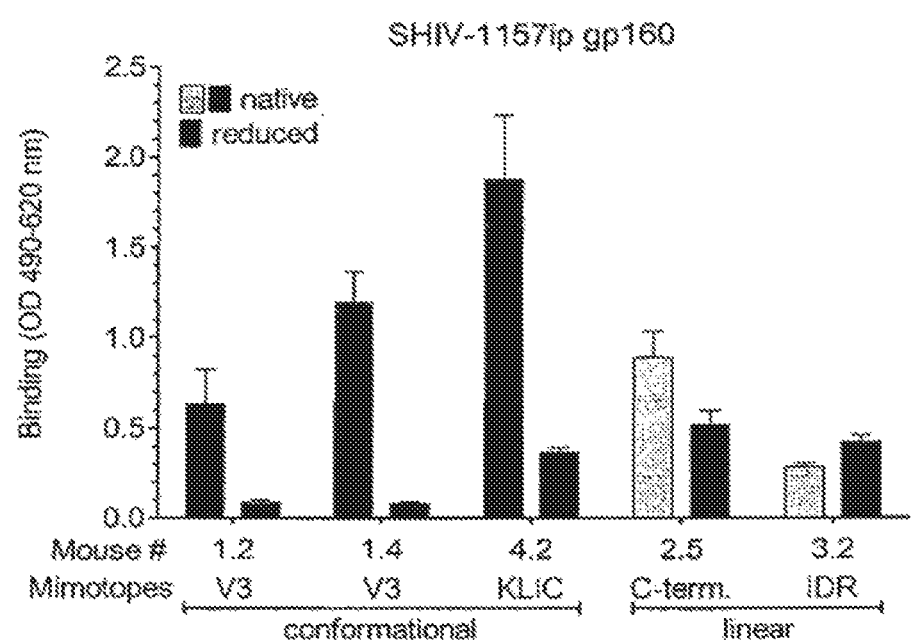

FIG. 8 Mouse immune sera were tested for binding to native (blue/orange bars) and reduced Env (black bars).

FIG. 9 illustrates additional HIV envelope like polypeptides useful according to the invention.

DETAILED DESCRIPTION

The invention provides methods, compositions and kits for treating and or preventing an HIV infection. For example, HIV envelope-like polypeptides (wild-type HIV polypeptides and mimotopes) may be administered to an individual so as to induce a protective immune response to HIV. Alternatively, antibodies directed to the HIV envelope-like polypeptides may be administered to an individual to treat or prevent an HIV infection and/or one or more symptoms associated with the infection (e.g., AIDS).

The present invention is based, at least in part, by the identification of neutralizing antibodies from rhesus macaques infected with SHIV-1157ip (a chimera that encodes env of a recently transmitted HIV-C strain) or the related SHIV-1157ipd3N4 [Song R J, et al. (2006). J Virol 80: 8729-8738]. These macaques developed high-titer neutralizing antibody (nAb) responses against homologous SHIV-clade C as well as heterologous primary strains of HIV-1 from different clades.

The humoral immune response of these rhesus monkeys with broadly reactive nAb responses was dissected using phage display. Recombinant phage peptide sequences were evaluated for conformational and linear homologies to gp160 using computational analysis [Schreiber A, et al. J Comput Chem 26: 879-887, 2005] with 3DEX software. 3DEX maps conformational mimotopes in 3D protein structures by using an algorithm that takes into account the physiochemical neighborhood of individual amino acids. These antibodies and HIV envelope-like polypeptides were utilized in various assays described herein. For example, it is taught herein that the HIV envelope-like polypeptides and antibodies to such polypeptides are useful in the prevention or treatment of HIV and one or more symptoms associated with HIV.

Definitions

"HIV" is meant to include HIV-1 (human immunodeficiency virus type-1), HIV-2 (human immunodeficiency virus type-2) and SIV (simian immunodeficiency virus). HIV includes but is not limited to extracellular virus particles and the forms of HIV associated with HIV infected cells. "HIV" is Human Immunodeficiency Virus, a virus that causes immunodeficiency by attacking $CD4^+$ cells in the body. HIV is organized into groups and subtypes (clades). Guidance on the application of the invention to different clades may also be found in HIV Sequence Compendium 2002 Kuiken C, Foley B, Freed E, Hahn B, Marx P, McCutchan F, Mellors J, Wolinsky S, and Korber B, editors. Published by the Theoretical Biology and Biophysics Group, Los Alamos National Laboratory, LA-UR number 03-3564, incorporated herein by reference. In particular, consensus sequence data for HIV-1 clades A, B, C and D and a number of isolates can be found on pages 490 to 550; consensus sequence data for HIV-2 clades A, B, C and D and a number of isolates can be found one pages 554 to 578.

As used herein, the terms "Env polypeptide" or "envelope polypeptide" refers to a molecule derived from an HIV envelope protein, e.g. (SEQ ID NO:93). The envelope protein of HIV is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of the virion, while the gp120 segment protrudes into the surrounding environment. Env polypeptides can exist as monomers, dimers or multimers.

As used herein, an "HIV envelope-like polypeptide" refers to a polypeptide derived from and envelope polypeptide of HIV. HIV envelope-like polypeptides include both wild-type polypeptides (naturally occurring, e.g., isolated from HIV infected patients) and mimotopes. For example, HIV envelope-like polypeptides include those illustrated in FIG. 1. Additional HIV envelope like polypeptides are known in the art.

A "gp120 polypeptide" is a molecule derived from a gp120 region of a Env polypeptide (e.g., corresponding to amino acid residues 1-511 of SEQ ID NO:93 The amino acid sequence of gp120 is approximately 511 amino acids. gp120 contains five relatively conserved domains interspersed with five variable domains (V1-V5). The variable domains contain extensive amino acid substitutions, insertions and deletions. A "gp120 polypeptide" includes both single subunits and multimers.

An "HIV V3 region" is the third of five variable loop regions of gp120 and is involved in viral infectivity by binding to a cytokine receptor (e.g., CCR5 or CXCR4) on the cellular target. The HIV V3 regions are known in the art and described herein. For example, an HIV V3 region corresponds to amino acid residues 296-331 of SEQ ID NO:93.

An "HIV C-terminal envelope region" is the C-terminal portion of the gp120 protein of HIV. C-terminal envelope polypeptides are known in the art and described herein. The C-terminal envelope region of HIV corresponds to amino acid residues ~485-509 of SEQ ID NO:93.

As used herein, a "mimotope" is a polypeptide, which differs from an envelope polypeptide by one or more amino acids but which mimics the three dimensional structure of a wild-type envelope epitope. A mimotope—generally in the context of a larger protein backbone called carrier—is able to stimulate a host's immune system to make an antibody antigen-specific response that generates antibodies that specifically bind to the mimotope and the corresponding wild-type envelope epitope. Mimotopes of the invention include the polypeptides of SEQ ID Nos: 1-84. Mimotopes of the invention also include the polypeptides presented in FIG. 9.

As used herein, "antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. Antigens of the present invention include the polypeptides of FIG. 1.

As used herein, an "antibody" includes any reactive fragment or fragments of antibodies such as Fab molecules, Fab proteins, single chain polypeptides, or the multifunctional antibodies having binding affinity for an antigen. The term includes chimeric antibodies, altered antibodies, univalent antibodies, bi-specific antibodies, monoclonal antibodies, polyclonal antibodies, human antibodies and humanized antibodies. Methods for preparing antibodies are well known in the art and described herein. A "neutralizing antibody" is an antibody that prevents HIV infection of target cells.

The term "specifically binds" means a high avidity and/or high affinity binding of an antibody to a specific antigen (e.g., HIV env). Antibody binding to its epitope on this specific antigen is stronger than binding of the same antibody to any other epitope (with the general exception of a wild-type HIV env and its corresponding mimotope), particularly those which may be present in molecules in association with, or in the same sample, as the specific antigen of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g., by use of appropriate controls.

A "humoral immune response" or "antibody immune response" refers to an immune response mediated by antibody molecules, while a "cellular immune response" is one mediated by T lymphocytes and/or other white blood cells. The antigen of interest may elicit an antibody-mediated immune response. Hence, an immunological response may include one or more of the following effects: the production of antibodies by B cells; and/or the activation of suppressor, cytotoxic, or helper T cells and/or T cells directed specifically to an antigen or antigens present in the composition or vaccine of interest. These responses may serve to neutralize infectivity, and/or mediate antibody-mediated complement lysis, or antibody dependent cell cytotoxicity (ADCC) to provide protection to an immunized host. Such responses can be determined using standard immunoassays and neutralization assays which are well known in the art.

As used herein, "isolated" when referring to a polynucleotide or a polypeptide, that the indicated molecule is separate and discrete from the whole organism with which the molecule is found in nature or, when the polynucleotide or polypeptide is not found in nature, is sufficiently free of other biological macromolecules so that the polynucleotide or polypeptide can be used for its intended purpose.

The term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and unnaturally occurring amino acids prepared by organic synthesis or other metabolic routes.

A "conservative amino acid substitution" is one in which the amino acid residue is replaced with an amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Other conserved amino acid substitutions can also occur across amino acid side chain families, such as when substituting an asparagine for aspartic acid in order to modify the charge of a peptide.

As used herein a "polypeptide" is a molecular chain of amino acids and does not refer to a specific length of the product. Thus, peptides, oligopeptides dimers, multimers, and the like are included within the definition of polypeptide. This term is also intended to include polypeptides that have been subjected to post-expression modifications such as, for example, glycosylations, acetylations, phosphorylations and the like. Furthermore, for purposes of the present invention, a "polypeptide" refers to a protein that includes modifications, such as deletions, additions and substitutions (generally conservative in nature), to the native sequence, as long as the protein maintains the desired activity.

As used herein, the terms "identity" or "percent identity", refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. The identity between two sequences is a direct function of the number of matching or identical positions. Thus, if a portion of the reference sequence is deleted in a particular peptide, that deleted section is not counted for purposes of calculating sequence identity. Identity is often measured using sequence analysis software e.g., BLASTN or BLASTP (available at the world wide web site ("www") of the National Center for Biotechnology Information (".ncbi") of the National Institutes of Health (".nih") of the U.S. government (".gov"), in the "Blast" directory ("/BLAST/"). The default parameters for comparing two sequences (e.g., "Blast"-ing two sequences against each other), by BLASTN (for nucleotide sequences) are reward for match=1, penalty for mismatch=−2, open gap=5, extension gap=2. When using BLASTP for protein sequences, the default parameters are reward for match=0, penalty for mismatch=0, open gap=11, and extension gap=1. Additional, computer programs for determining identity are known in the art.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection.

Figure 1:
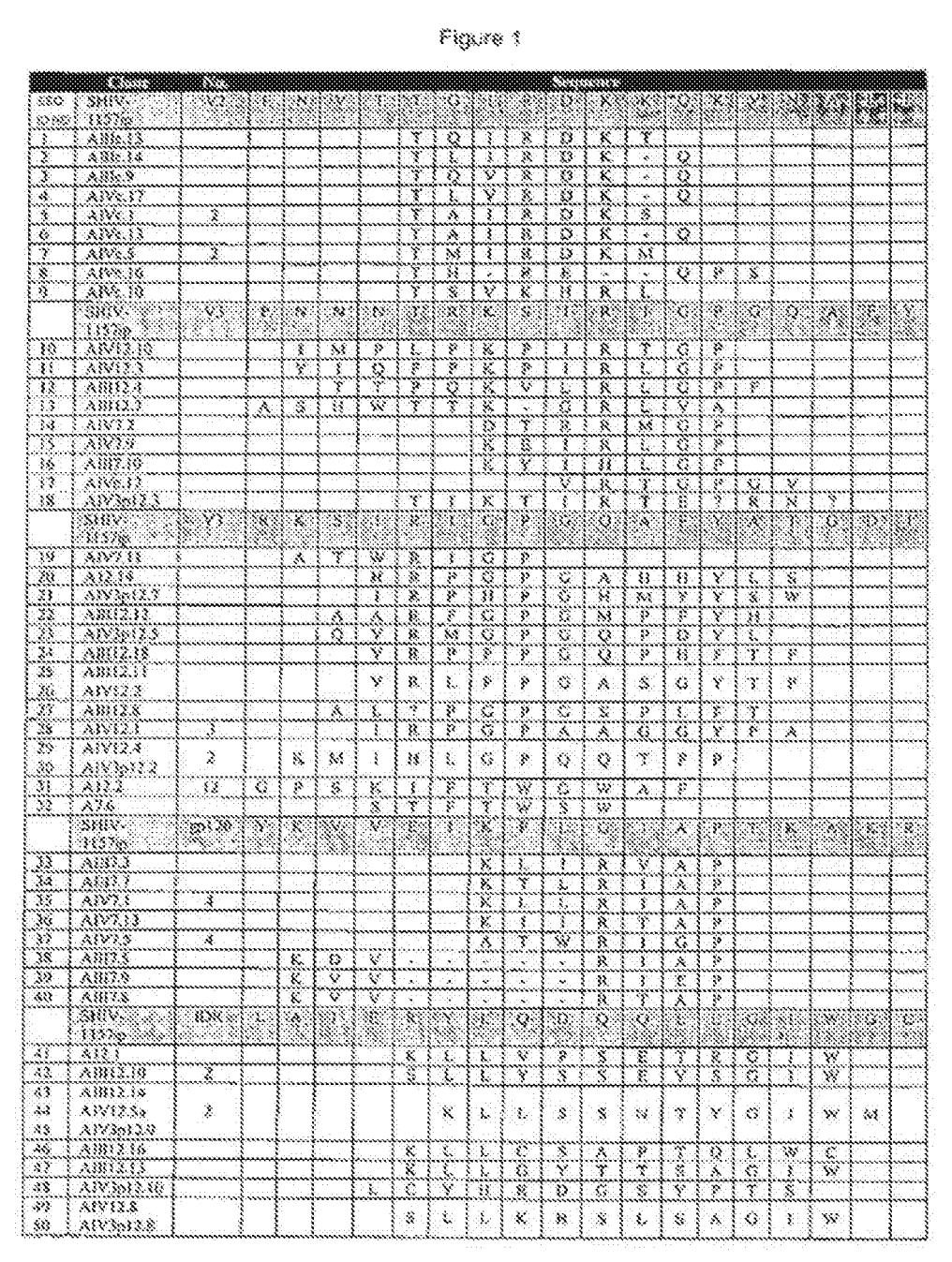
Figure 1:
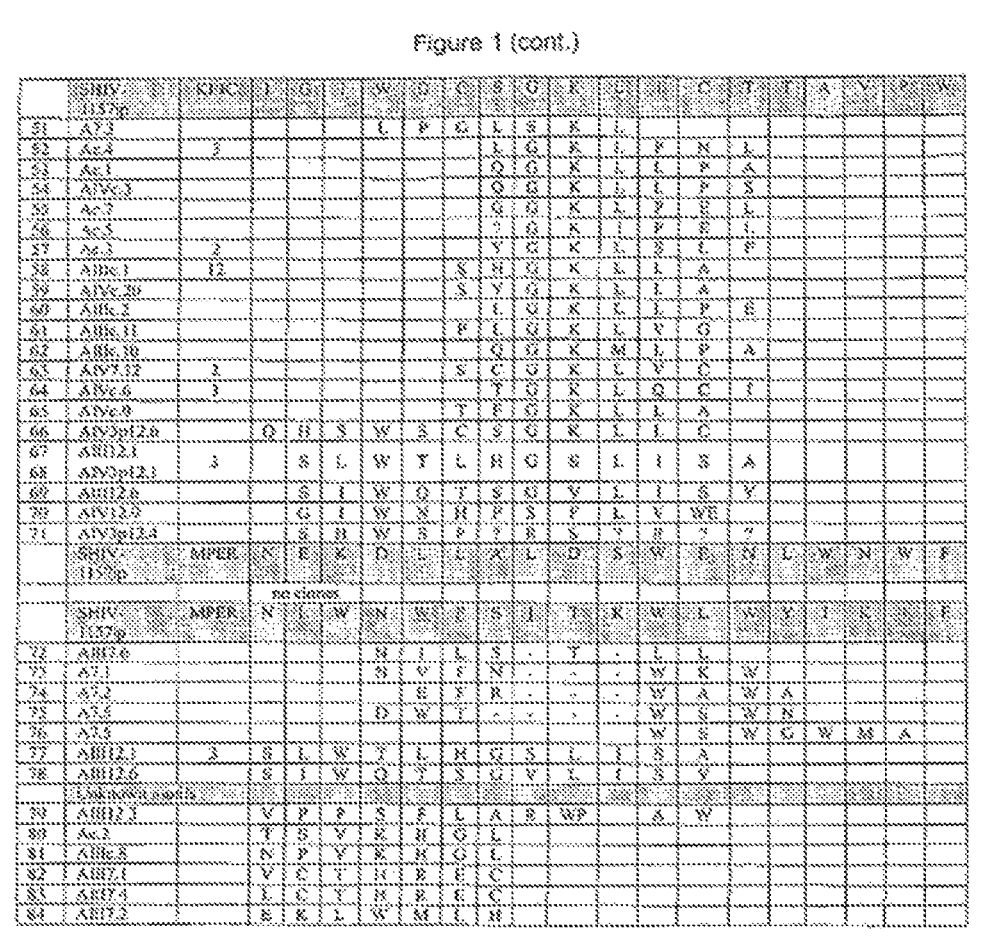

In one aspect, the invention is directed to an isolated HIV envelope-like polypeptide. Generally, the HIV envelope-like polypeptide has an amino acid sequence which is 80% or more identical to an amino acid sequence depicted in FIG. 1. Suitable HIV envelope-like polypeptides include both mimotope and wild-type HIV envelope polypeptides (gp160). In some embodiments, the HIV envelope-like polypeptides have an amino acid sequence which is 85%, 90%, 95%, 96%, 97%, 98%, 99% or more identical to an amino acid sequence depicted in FIG. 1 (SEQ ID NOs: 1-84). In a preferred embodiment, the HIV envelope-like polypeptide has an amino acid sequence which is identical to an amino acid sequence depicted in FIG. 1. HIV envelope-like peptides which are mimotopes are illustrated in FIG. 1 as SEQ ID NOs: 1-84; of these SEQ ID NOs: 21, 23, 25, 28, 29 and 31 correspond to the HIV V3 envelope region and SEQ ID NOs: 34, 35, 37, 38 and 39 correspond to the HIV envelope C-terminal region. The HIV envelope-like polypeptides may also be wild-type HIV envelope proteins, for example, peptides that are 80% or more identical to SEQ ID NOs: 85-92. In some instances, the HIV envelope-like polypeptide may be a fusion polypeptide, e.g., mimotope linked to a carrier polypeptide.

The invention is also directed to nucleic acids encoding the HIV envelope-like polypeptides. Generally, the nucleic acids encode HIV envelope-like polypeptides having an amino acid sequence which is 80% or more identical to an amino acid sequence depicted in FIG. 1. Suitable HIV envelope-like polypeptides include both mimotope and wild-type HIV envelope polypeptides (gp160). In some embodiments, the nucleic acids encode HIV envelope-like polypeptides having an amino acid sequence which is 85%, 90%, 95%, 96%, 97%, 98%, 99% or more identical to an amino acid sequence depicted in FIG. 1. In a preferred embodiment, the nucleic acid encodes an envelope-like polypeptide having an amino acid sequence which is identical to an amino acid sequence depicted in FIG. 1. HIV envelope-like peptides which can be characterized as mimotopes are illustrated in FIG. 1 as SEQ ID NOs: 1-84; of these SEQ ID NOs: 21, 23, 25, 28, 29 and 31 correspond to the HIV V3 envelope region and SEQ ID NOs: 34, 35, 37, 38 and 39 correspond to the HIV envelope C-terminal region. The nucleic acids may encode HIV envelope-like polypeptides which are wild-type HIV envelope proteins, for example, peptides that are 80% or more identical to SEQ ID NOs: 85-92. In some instances, the nucleic acid encodes a HIV envelope-like polypeptide which is a fusion polypeptide, e.g., mimotope linked to a carrier polypeptide. The nucleic acids may be isolated, in a vector or expressed in a host cell.

In yet another aspect the invention is directed to an antibody that specifically binds to an HIV envelope-like polypeptide. Generally, the antibody will bind to a HIV envelope-like polypeptide having an amino acid sequence which is 80% or more identical to an amino acid sequence depicted in FIG. 1. Suitable antibodies bind to HIV envelope-like polypeptides, including mimotope and wild-type HIV envelope polypeptides (gp160). In some embodiments, the antibodies bind to HIV envelope-like polypeptides which have an amino acid sequence which is 85%, 90%, 95%, 96%, 97%, 98%, 99% or more identical to an amino acid sequence depicted in FIG. 1. In a preferred embodiment, the antibody binds to an envelope-like polypeptide having an amino acid sequence which is identical to an amino acid sequence depicted in FIG. 1. In one embodiment, the antibody binds to a mimotope of an HIV envelope peptide such as those illustrated in SEQ ID NOs: 1-84. More specifically the antibody may bind to a mimotope of the HIV V3 envelope region, wherein the mimotope has the amino acid sequence of SEQ ID NOs: 21, 23, 25, 28, 29 and 31. The antibodies of the invention may bind to HIV envelope-like peptides which correspond to the HIV envelope C-terminal region, e.g., SEQ ID NOs: 34, 35, 37, 38 and 39. The antibodies may also be specific for and bind to wild-type HIV envelope proteins, for example, peptides that are 80% or more identical to SEQ ID NOs: 85-92.

The antibodies may be derived from a vertebrate such as a mouse, human or monkey and can be either polyclonal or monoclonal. Chimeric and humanized antibodies as well as binding fragments (e.g. Fab fragment) are also contemplated.

Further, any of the above HIV envelope-like polypeptides, nucleic acids and antibodies may be included in a kit or composition, e.g., pharmaceutical composition.

The invention is also directed to methods for inducing an immune response in a subject by administering a pharmaceutical composition having an immunologically effective dose of one or more HIV envelope-like polypeptides. Generally, the HIV envelope-like polypeptide is 80% or more identical to an amino acid sequence of FIG. 1. Suitable HIV envelope-like polypeptides include both mimotope and wild-type HIV envelope polypeptides (gp160). In some embodiments, the HIV envelope-like polypeptide has an amino acid sequence which is 85%, 90%, 95%, 96%, 97%, 98%, 99% or more identical to an amino acid sequence depicted in FIG. 1. In a preferred embodiment, the subject is administered one or more envelope-like polypeptides having an amino acid sequence which is identical to an amino acid sequence depicted in FIG. 1. Peptides suitable for inducing a protective immune response include HIV envelope-like peptides having the amino acid sequence of SEQ ID NOs: 1-84, of these SEQ ID NOs: 21, 23, 25, 28, 29 and 31 correspond to HIV V3 envelope region SEQ ID NOs: 34, 35, 37, 38 and 39 correspond to the HIV envelope C-terminal region. Alternatively, the HIV envelope-like polypeptides included in the pharmaceutical composition may be wild-type HIV envelope proteins, for example, peptides that are 80% or more identical to SEQ ID NOs: 85-92. Preferably, the HIV envelope-like polypeptide is fusion polypeptide, e.g., mimotope-carrier fusion polypeptide. In some embodiments, the method of inducing an immune response includes the sequential or co-administration of a nucleic acid encoding a HIV envelope polypeptide (e.g., gp160).

Administering a therapeutically effective dose of an antibody that specifically binds to an HIV envelope-like polypeptide may also be used as a means for treating or preventing an HIV infection in a subject. Generally, the HIV envelope like polypeptide has an amino acid sequence which is 80% or more identical to an amino acid sequence depicted in FIG. 1. Suitable antibodies bind to HIV envelope-like polypeptides include both mimotope and wild-type HIV envelope polypeptides (gp160). In some embodiments, the antibodies bind to HIV envelope-like polypeptides having an amino acid sequence which is 85%, 90%, 95%, 96%, 97%, 98%, 99% or more identical to an amino acid sequence depicted in FIG. 1. In a preferred embodiment, the antibody binds to an envelope-like polypeptide having an amino acid sequence which is identical to an amino acid sequence depicted in FIG. 1. In one embodiment, the antibody binds to a mimotope of an HIV envelope peptide such as those illustrated in SEQ ID NOs: 1-84. More specifically the antibody binds to a mimotope of the HIV V3 envelope region, wherein the mimotope has an amino acid sequence which is 80% or more identical to SEQ ID NOs: 21, 23, 25, 28, 29 and 31. In another embodiment, the antibody used in the method of treatment is a mimotope derived from the HIV C-terminal envelope region and has an amino acid sequence which is 80% or more identical to the amino acid sequence of SEQ ID NOs: 34, 35, 37, 38 and 39. The antibodies used in the method may also be specific for and bind to wild-type HIV envelope proteins, for example, peptides that are 80% or more identical to SEQ ID NOs: 85-92.

The antibodies may be derived from a vertebrate such as a mouse, human or monkey and can be either polyclonal or monoclonal. Chimeric and humanized antibodies as well as binding fragments (e.g. Fab fragment) are also contemplated.

In yet another aspect, the invention is directed to a cell line that produces an antibody which specifically binds to one or more of SEQ ID NOs 1-84.

HIV Envelope-Like Polypeptides and Polynucleotides

Certain aspects of the invention are directed to isolated HIV envelope-like polypeptides and nucleic acids encoding the polypeptides. Generally, the HIV envelope-like polypeptide has an amino acid sequence which is 80% or more identical to an amino acid sequence depicted in FIG. 1. Suitable HIV envelope-like polypeptides include both mimotope and wild-type HIV envelope polypeptides (gp160). In some embodiments, the HIV envelope-like polypeptides have an amino acid sequence which is 85%, 90%, 95%, 96%, 97%, 98%, 99% or more identical to an amino acid sequence depicted in FIG. 1 (SEQ ID NOs: 1-84). In a preferred embodiment, the HIV envelope-like polypeptide has an amino acid sequence which is identical to an amino acid sequence depicted in FIG. 1. HIV envelope-like peptides which are mimotopes are illustrated in FIG. 1 as SEQ ID NOs: 1-84; of these SEQ ID NOs: 21, 23, 25, 28, 29 and 31 correspond to the HIV V3 envelope region and SEQ ID NOs: 34, 35, 37, 38 and 39 correspond to the HIV envelope C-terminal region. The HIV envelope-like polypeptides may also be wild-type HIV envelope proteins, for example, peptides that are 80% or more identical to SEQ ID NOs: 85-92. In some instances, the HIV envelope-like polypeptide may be a fusion polypeptide, e.g., mimotope linked to a carrier polypeptide.

A polynucleotide of the present invention may be employed for producing a polypeptide by recombinant techniques. Such a polypeptide may be useful, for example, as an antigen for the induction of an immune response specific to HIV or as a reagent for the affinity purification of an antibody to HIV.

The relatively small HIV envelope-like polypeptides, i.e., up to about 50 amino acids in length, can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis. Synthesis. Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis, Synthesis, Biology, Vol. 1, for classical solution synthesis.

The polypeptides of the present invention can also be chemically prepared by other methods such as by the method of simultaneous multiple peptide synthesis. See, e.g., Houghten Proc. Natl. Acad. Sci. USA (1985) 82:5131-5135; U.S. Pat. No. 4,631,211.

The polypeptides of the invention can also be synthesized using recombinant techniques, well known in the art. In this regard, oligonucleotide probes can be devised based on the known sequences of HIV Env polypeptides and used to probe virus, HIV infected cells or cDNA libraries for HIV envelope-like polypeptide genes. The gene can then be further isolated using standard techniques and, e.g., restriction enzymes employed to truncate the gene at desired portions of the full-length sequence. Similarly, the HIV envelope-like peptide gene(s) can be isolated directly from cells and tissues infected with HIV, using known techniques, such as phenol extraction and the sequence further manipulated to produce the desired truncations. See, e.g., Sambrook et al., supra, for a description of techniques used to obtain and isolate DNA.

The genes encoding the HIV envelope-like peptides (e.g., full length and fragments) polypeptides can be produced synthetically, based on the amino acid sequences disclosed herein. The nucleotide sequence can be designed with the appropriate codons for the particular amino acid sequence desired. If large, the complete sequence is can be assembled from overlapping oligonucleotides prepared by standard methods and assembled into a complete coding sequence.

See, e.g., Edge (1981) Nature 292:756; Nambair et al. (1984) Science 223:1299; Jay et al. (1984) J. Biol. Chem. 259:6311; Stemmer et al. (1995) Gene 164:49-53.

Recombinant techniques are readily used to clone a gene encoding an HIV envelope-like polypeptide which can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer which hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, Methods Enzymol. (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. Proc. Natl. Acad. Sci USA (1982) 79:6409.

Once coding sequences for the desired proteins have been isolated or synthesized, they can be cloned into any suitable vector or replicon for expression. A wide variety of vectors encoding modified polypeptides can be generated by creating expression constructs which operably link the polynucleotides of the invention. The construct is then introduced into a host cell for polypeptide expression. Preferably, the HIV envelope-like polypeptides are fusion polypeptides linked to an immuno-carrier protein.

Immunocarriers include polypeptides such as ankyrin repeat domains, C3d, influenza virus, albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein-derived or non-protein derived substances are known to those skilled in the art.

Numerous cloning vectors are known to those of skill in the art, and the selection of an appropriate cloning vector is a matter of choice. Examples of recombinant DNA vectors for cloning and host cells which they can transform include the bacteriophage λ, (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells).

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("FastBac" kit).

Viral systems, such as a vaccinia based infection/transfection system, as described in Tomei et al., J. Virol. (1993) 67:4017-4026 and Selby et al., J. Gen. Virol. (1993) 74:1103-1113, will also find use with the present invention. In this system, cells are first transfected in vitro with a vaccinia virus recombinant that encodes the bacteriophage T7 RNA polymerase. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired HIV envelope-like peptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Depending on the expression system and host selected, the proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, a γ-interferon signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the HIV clade C envelope polypeptide substantially intact. Intracellular proteins can also be obtained by removing components from the cell wall or membrane, e.g., by the use of detergents or organic solvents, such that leakage of the Env polypeptides occurs. Such methods are known to those of skill in the art and are described in, e.g., Protein Purification Applications: A Practical Approach, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced Env polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining an intracellular HIV envelope-like peptide of the present invention involves affinity purification, such as by immunoaffinity chromatography using anti-Env specific antibodies, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the HIV envelope-like polypeptides can be further purified using conventional techniques well known in the art, such as by any of the techniques described above.

Antibodies

In yet another aspect the invention is directed to an antibody that specifically binds to an HIV envelope-like polypeptide. Generally, the antibodies that bind the HIV envelope-like polypeptides have an amino acid sequence which is 80% or more identical to an amino acid sequence depicted in FIG. 1.

The present invention provides antibodies that may differentially or preferentially bind to one or more epitopes on HIV envelope. Antibodies of the invention include, but are not limited to, monoclonal antibodies, monospecific antibodies, polyclonal antibodies, multispecific antibodies, diabolizes, triabodies, tetrabodies, human antibodies, humanized antibodies, camelized antibodies, chimeric antibodies, single chain antibodies, single domain antibodies, Fab fragments, F(ab') fragments, $F(ab')_2$ fragments, Fv fragments (i.e., the smallest functional module of an antibody), single chain Fvs (scFv), disulfide-stabilized Fvs (dsFv), Fd, $V_H$, $V_L$, $V_\alpha$, $V_\beta$, and anti-idiotypic (anti-Id) antibodies (including, e.g., anti-Id antibodies to antibodies of the invention), intrabodies, and epitope-binding fragments of any of the above. In some embodiments, the antibodies are monoclonal antibodies. In other embodiments, the antibodies are Fv fragments, including $V_H$ and $V_L$ regions.

In particular, antibodies of the present invention include immunoglobulin molecules and immunologically active portions of immunoglobulin molecules, i.e., molecules that contain an antigen binding site that binds to a HIV envelope antigen. The immunoglobulin molecules of the invention can be of any type (e.g., IgG, IgE, IgM, IgD, IgA, and IgY), class (e.g., $IgG_1$, $IgG_2$, $IgG_3$, $IgG_4$, $IgA_1$, and $IgA_2$), or subclass of immunoglobulin molecule. In a specific embodiment, an antibody of the invention is an IgG antibody. In another specific embodiment, an antibody of the invention is not an IgA antibody.

The antibodies of the invention may be from any animal origin including birds and mammals (e.g., human, mouse, donkey, sheep, rabbit, goat, guinea pig, camel, horse, or chicken). Preferably, the antibodies of the invention are human or humanized monoclonal antibodies. As used herein, “human” antibodies include antibodies having the amino acid sequence of a human immunoglobulin and include antibodies isolated from human immunoglobulin libraries or from mice that express antibodies from human genes.

The antibodies of the present invention may be monospecific, bispecific, trispecific, or of greater multispecificity. Multispecific antibodies may be specific for different epitopes of a HIV envelope-like polypeptide. See, e.g., PCT publications WO 93/17715, WO 92/08802, WO 91/00360, and WO 92/05793; Tutt, et al., *J. Immunol.* 147:60-69 (1991); U.S. Pat. Nos. 4,474,893, 4,714,681, 4,925,648, 5,573,920, and 5,601,819; and Kostelny, et al., J Immunol 148:1547-1553 (1992).

In one embodiment, antibodies of the invention bind to cells that express HIV envelope antigens. In a specific embodiment, antibodies of the invention bind to a fragment of HIV envelope comprising 8 to 285, 8 to 275, 8 to 250, 8 to 200, 8 to 175, 8 to 150, 8 to 100, 8 to 50, 8 to 25, 15 to 50, 15 to 75, 15 to 100 or 15 to 150 amino acids of HIV envelope. Preferably, the antibodies bind to the polypeptides represented by SEQ ID NOs 1-94.

An antibody of the invention may be composed of one or two polypeptide chains. In one embodiment, an Fv antibody that binds to an HIV envelope-like polypeptide is composed of a single polypeptide chain, where the $V_H$ region is bound by an amino acid linker to the $V_L$ chain region. In a preferred embodiment, such scFvs are stable at 37° C. for about 2 minutes, 5 minutes, 10 minutes, 15 minutes, 20 minutes, 25 minutes, 30 minutes, 1 hour, 1.5 hours, 2 hours, 3 hours, 4 hours, 5 hours, 6 hours, 7 hours, 12 hours, 14 hours, 24 hours, 48 hours, 1 week, 2 weeks, 1 month, 3 months, 6 months, 1 year or longer as assessed by a technique known to one of skill in the art or described herein. In another embodiment, the $V_H$ region of an Fv antibody that binds to 67LR is bound to a $V_L$ chain region through at least one disulfide linkage (e.g., formed between respective cysteines in each chain). In certain embodiments, the disulfide linked Fv chains have a reduced tendency to aggregate as measured by, e.g., HPLC, and have a longer serum half-life. Thus, in a specific embodiment, a disulfide-stabilized Fv (dsFv) antibody comprises at least two polypeptides linked by at least one disulfide linkage. The two polypeptides can be separated by a termination codon and downstream initiation codon and ribosome binding site, so that the chains are encoded as separate open reading frames, or they can be additionally joined by a peptide linker. In order to provide disulfide covalent bonds between the $V_H$ and $V_L$ chains of dsFv fragments, cysteine residues are necessary. Cysteine residues can be introduced in the proper position of each $V_H$ and $V_L$, determined by alignment to reference sequences, by standard molecular biology techniques (e.g., site directed mutagenesis). See Pastan, et al., U.S. Pat. No. 6,147,203, which is incorporated by reference herein in its entirety, especially columns 5-7.

In another embodiment, the $V_L$ and $V_H$ sequences will be followed respectively by part or all of the light and heavy chain constant regions, e.g., the whole kappa light chain constant region and the $C_{H1}$ domain of the heavy chain constant region, with or without the heavy chain hinge domain. Thus, the genes encoding the antibody segments may occur in any order on a single plasmid, or may be expressed separately from separate plasmids. For example, in another embodiment of the invention, the $V_L$ gene and any light chain constant region will be on one plasmid, while the $V_H$ gene and any heavy chain constant region will be on a second plasmid. In either case, the $V_L$ and/or $V_H$ genes may be preceded by a signal sequence that directs the secretion of the recombinant fusion protein from the cell. See, e.g., U.S. Pat. Nos. 6,147,203, 6,074,644, 6,051,405 which are incorporated herein by reference in their entirety.

In another embodiment, the invention provides for single chain antibodies, in which the antibody comprises the $V_L$ or $V_H$ regions alone, rather than as components of Fv fragments. See, e.g., U.S. Pat. No. 6,074,644, which is incorporated herein by reference in its entirety.

An antibody can also be conjugated to a second antibody to form an antibody heteroconjugate as described by Segal in U.S. Pat. No. 4,676,980, which is incorporated herein by reference in its entirety. In a specific embodiment, two or more antibodies are cross-linked to each to produce a bispecific or multispecific antibody.

In one embodiment, antibodies with high affinity and specificity are chosen for conjugation to a cytotoxic agent, and they are then assessed for their ability to selectively and potently kill HIV or HIV infected cells.

Those skilled in the art will realize that additional modifications, deletions, insertions and the like may be made to the antibodies directed to HIV envelope-like polypeptides. Especially, deletions or other changes may be made to the antibody in order to increase stability, affinity, specificity, or, when combined with a cytotoxic agent, cytotoxicity. Typical modifications include, but are not limited to, introduction of an upstream methionine for transcription initiation, mutation of residues to cysteine in $V_H$ or $V_L$ regions for the creation of disulfide linkages, etc. All such constructions may be made by methods of genetic engineering well known to those skilled in the art. Fragments, analogs, and derivatives of antibodies to HIV envelope-like polypeptides can be useful in the present invention provided that when fused to a cytotoxic agent portion of the conjugate, such fragments, analogs, and derivatives maintain the ability to bind native envelope expressed on the surface of a cell or HIV particle. Preferably, the binding kinetics of the fragments, analogs, or derivatives remain the same or vary by no more than 25% (preferably, no more than 15%, 10% or 5%) as determined by an assay described herein.

To improve or alter the characteristics of antibodies to HIV envelope-like polypeptides, protein engineering may be employed. Recombinant DNA technology known to those skilled in the art can be used to create novel mutant proteins or "muteins" including single or multiple amino acid substitutions, deletions, additions, or fusion proteins. Such modified polypeptides can show, e.g., enhanced activity or increased stability. In addition, they may be purified in higher yields and show better solubility than the corresponding natural polypeptide, at least under certain purification and storage conditions. For instance, for many proteins, it is known in the art that one or more amino acids may be deleted from the amino terminus or carboxy terminus without substantial loss of biological function.

Antibodies may be altered by random mutagenesis by error-prone PCR, random nucleotide insertion or other methods prior to recombination.

The antibodies of the invention include derivatives that are modified, i.e., by the covalent attachment of any type of molecule to the antibody such that covalent attachment does not adversely affect binding to the antigen or, in the case of antibody conjugates of the invention, adversely affect its ability to bind to HIV envelope and adversely affect its ability to kill HIV or a cell infected with HIV or inhibit transmission of HIV. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The present invention also provides antibodies that bind to HIV envelope-like polypeptides that comprise a framework region known to those of skill in the art (e.g., a human or non-human fragment). The framework region may be naturally occurring or consensus framework regions. In one embodiment, the framework region of an antibody of the invention is human (see, e.g., Clothia, et al., 1998, J Mol Biol 278:457-479 for a listing of human framework regions, which is incorporated by reference herein in its entirety).

In a specific embodiment, the present invention provides for antibodies that bind to HIV envelope-like polypeptides, said antibodies comprising the amino acid sequence of the antibodies produced by hybridoma cell lines and human murine framework regions. In another embodiment, the present invention provides for antibodies that bind to HIV envelope-like polypeptides, said antibodies comprising the amino acid sequence of antibodies produced by hybridoma cell lines and human or murine framework regions with one or more amino acid substitutions at one, two, three, or more of the following residues: (a) rare framework residues that differ between the murine antibody framework (i.e., donor antibody framework) and the human antibody framework (i.e., acceptor antibody framework); (b) Venier zone residues when differing between donor antibody framework and acceptor antibody framework; (c) interchain packing residues at the $V_H/V_L$ interface that differ between the donor antibody framework and the acceptor antibody framework; (d) canonical residues that differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the $V_H$ domain and the $V_L$ domain.

The present invention also provides antibodies that bind to HIV envelope-like polypeptides that comprise constant regions known to those of skill in the art. In one embodiment, the constant regions of an antibody of the invention are human. In another embodiment, the constant regions are murine.

The present invention provides for antibodies that bind to HIV envelope-like polypeptides, the antibodies having an extended half-life in vivo and the use of such antibodies. To prolong the serum circulation of antibody conjugates (e.g., monoclonal antibodies, single chain antibodies, Fv fragments, and Fab fragments) in vivo, for example, inert polymer molecules such as high molecular weight polyethylene glycol (PEG) can be attached to the antibodies with or without a multifunctional linker either through site-specific conjugation of the PEG to the amino or carboxyl terminus of the antibodies (whichever end is not conjugated to the cytotoxic agent) or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or ion-exchange chromatography. Polyethylene glycol-derivatized antibodies can be tested for binding activity as well as for in vivo efficacy using methods well-known to those of skill in the art, for example, by immunoassays described herein.

Antibodies having an increased half-life in vivo can also be generated by introducing one or more amino acid modifications (i.e., substitutions, insertions, or deletions) into an IgG constant domain, or FcRn binding fragment thereof (preferably a Fc or hinge Fc domain fragment). See, e.g., International Publication No. WO 98/23289; International Publication No. WO 97/34631; International Publication No. WO 02/060919; and U.S. Pat. No. 6,277,375, each of which is incorporated herein by reference in its entirety.

Furthermore, antibodies can be conjugated to albumin in order to make the antibody more stable in vivo or have a longer half-life in vivo. The techniques are well-known in the art; see, e.g., International Publication Nos. WO 93/15199, WO 93/15200, and WO 01/77137; and European Patent No. EP 413,622, all of which are incorporated herein by reference.

Methods for Producing Antibodies

Antibodies that bind to an antigen can be produced by any method known in the art for the synthesis of antibodies, in particular, by chemical synthesis or preferably, by recombinant expression techniques.

Polyclonal antibodies specific for an antigen can be produced by various procedures well-known in the art. As a non-limiting example, the antigen (i.e., HIV envelope-like polypeptides) can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Köhler & Milstein, 1975, Nature 256:495-497; Pasqualini & Arap, 2004, PNAS USA 101:257-259; Steinitz, et al., 1977, Nature 269:420-422; Vollmers, et al., 1989, Cancer Res 49:2471-2476; Vollmers & Brandlein, 2002 Hum. Antibodies 11(4): 131-142; Harlow, et al., Antibodies: A Laboratory Manual, (Cold Spring Harbor Laboratory Press, 2nd ed. 1988); Hammerling, et al., in: Monoclonal Antibodies and T Cell Hybridomas 563 681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding HIV envelope-like polypeptides. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments that recognize specific HIV envelope-like polypeptides may be generated by any technique known to those of skill in the art. For example, total cellular RNA is isolated from hybridoma cells expressing the desired monoclonal antibodies using methods known to those skilled in the art, e.g., using the Qiagen RNeasy mini kit. $V_H$ and $V_L$ cDNAs of the monoclonal antibodies can be obtained by a RACE method using SMART RACE cDNA amplification kit (Clontech) as described in Pastan, et al., Methods Mol Biol 2004; 248:503-18, or other method for preparation of cDNA known to those of skill in the art. Prepared cDNAs are then used as the template for PCR reactions to amplify the desired $V_H$ and $V_L$ fragments. The PCR products can then be cloned into an appropriate vector, either directly into a vector containing the cytotoxin, or transferred to a shuttle vector, such as pCR4®-TOPO®, using the TOPO TA cloning kit (Invitrogen). The $V_H$ and $V_L$ chains can then be assembled into a single chain Fv (scFv) and fused to a cytotoxin as described in Pastan, et al., Methods Mol Biol 2004; 248:503-18, which is incorporated herein by reference in its entirety. As another example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $CH_1$ domain of the heavy chain.

Further, the antibodies of the present invention can also be generated using various phage display methods known in the art. In phage display methods, functional antibody domains are displayed on the surface of phage particles that carry the polynucleotide sequences encoding them. In particular, DNA sequences encoding $V_H$ and $V_L$ domains are amplified from animal cDNA libraries. The DNA encoding the $V_H$ and $V_L$ domains are recombined together with an scFv linker by PCR and cloned into a phagemid vector. The vector is electroporated into E. coli and the E. coli is infected with helper phage. Phage used in these methods are typically filamentous phage including fd and M13 and the $V_H$ and $V_L$ domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman, et al., 1995, J Immunol Methods 182:41-50; Ames, et al., 1995, J Immunol Methods 184:177-186; Kettleborough, et al., 1994, Eur J Immunol 24:952-958; Persic, et al., 1997, Gene 187:9-18; Burton, et al., 1994, Advances in Immunology 57:191-280; International application No. PCT/GB91/01134; Griffiths, et al., 1994, EMBO J 13:3245-3260; Winter, et al., 1994, Annu Rev Immunol 12:433-455; Liv, et al., 2004, Cancer Res 64:704-710; International publication Nos. WO 90/02809, WO 91/10737, WO 92/01047, WO 92/18619, WO 93/11236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT publication No. WO 92/22324; Mullinax, et al., 1992, BioTechniques 12(6):864-869; Sawai, et al., 1995, AJRI 34:26-34; and Better, et al., 1988, Science 240:1041-1043 (said references incorporated by reference in their entireties).

To generate whole antibodies, PCR primers including $V_H$ or $V_L$ nucleotide sequences, a restriction site, and a flanking sequence to protect the restriction site can be used to amplify the $V_H$ or $V_L$ sequences in scFv clones. Utilizing cloning techniques known to those of skill in the art, the PCR amplified $V_H$ domains can be cloned into vectors expressing a $V_H$ constant region, e.g., the human gamma 4 constant region, and the PCR amplified $V_L$ domains can be cloned into vectors expressing a $V_L$ constant region, e.g., human kappa or lambda constant regions. Preferably, the vectors for expressing the $V_H$ or $V_L$ domains comprise an EF-1α promoter, a secretion signal, a cloning site for the variable domain, constant domains, and a selection marker such as neomycin. The $V_H$ and $V_L$ domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use humanized antibodies or chimeric antibodies. Completely human antibodies and humanized antibodies are particularly desirable for therapeutic treatment of human subjects. Human antibodies can be made by a variety of methods known in the art including phage display methods described above using antibody libraries derived from human immunoglobulin sequences. See U.S. Pat. Nos. 4,444,887 and 4,716,111; and International publication Nos. WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice that are incapable of expressing functional endogenous immunoglobulins, but that can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM, and IgE antibodies. For an overview of this technology for producing human antibodies, see Lonberg and Huszar, 1995, Int. Rev. Immunol. 13:65 93.

For a detailed discussion of methods for producing human antibodies and human monoclonal antibodies and protocols for producing such antibodies, see, e.g., Tomizuka et al., 2000 PNAS USA 97:722-727; Davis, et al., 2004, Methods Mol Biol 248:191-200; Lagerkvist et al., 1995, Biotechniques 18:862-869; Babcook, et al., 1996 PNAS USA 93:7843-7848; International publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See e.g., Morrison, 1985, Science 229:1202; Oi, et al., 1986, BioTechniques 4:214; Gillies, et al., 1989, J Immunol Methods 125:191-202; and U.S. Pat. Nos. 5,807,715, 4,816,567, 4,816,397, and 6,311,415, which are incorporated herein by reference in their entirety.

A humanized antibody is an antibody that is capable of binding to a predetermined antigen and that comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')$_2$, Fabc, Fv), in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA, and IgE, and any isotype, including IgG1, IgG2, IgG3, and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%. A humanized antibody can be produced using variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Pat. No. 6,407,213, U.S. Pat. No. 5,766,886, International Publication No. WO 9317105, Tan, et al., J Immunol 169: 1119 25 (2002), Caldas, et al., Protein Eng 13(5):353 60 (2000), Morea, et al., Methods 20(3):267 79 (2000), Baca, et al., J Biol Chem 272(16):10678 84 (1997), Roguska, et al., Protein Eng 9(10):895 904 (1996), Couto, et al., Cancer Res 55 (23 Supp):5973s-5977s (1995), Couto, et al., Cancer Res 55(8):1717 22 (1995), Sandhu J S, Gene 150(2):409 10 (1994), and Pedersen, et al., J Mol Biol 235(3):959 73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen, et al., U.S. Pat. No. 5,585,089; and Riechmann, et al., 1988, Nature 332:323, which are incorporated herein by reference in their entireties.)

Diabodies, triabodies, and tetrabodies can be produced by techniques known to one of skill in the art. See, e.g., Kipriyanov, 2002, Methods Mol Biol 178:317-331; Todorovska, et al., 2001 J Immunol Methods 248:47-66; and Poljak, et al., 1994, Structure 2:1121-1123, each of which are incorporated herein by reference in their entirety, for methods for producing diabodies, triabodies, and tetrabodies. Single domain antibodies can also be produced by techniques known to one of skill in the art. For a description of techniques to produce single domain antibodies, see, e.g., Holliger & Hudson, 2005 Nat. Biotechnol. 23:1126-1136, Riechmann, et al., 1999, J Immunol Methods 231:25-38; and Dick, 1990, BMJ 300:659-600, each of which is incorporated herein by reference in its entirety. Generation of intrabodies is well-known to the skilled artisan and is described, for example, in U.S. Pat. Nos. 6,004,940; 6,072,036; 5,965,371, which are incorporated by reference in their entireties herein. Further, the construction of intrabodies is discussed in Ohage and Steipe, 1999, J. Mol. Biol. 291: 1119-1128; Ohage, et al., 1999, J Mol Biol 291:1129-1134; and Wirtz and Steipe, 1999, Protein Science 8:2245-2250, which references are incorporated herein by reference in their entireties. Recombinant molecular biological techniques such as those described for recombinant production of antibodies may also be used in the generation of intrabodies.

Nucleic Acids Encoding Antibodies

The invention provides nucleic acid sequences comprising a nucleotide sequence encoding an antibody or an antibody conjugate that binds to HIV envelope-like polypeptides. In a specific embodiment, such nucleic acid sequences are isolated. The invention also encompasses nucleic acid sequences that hybridize under high, intermediate, or lower stringency hybridization conditions, e.g., as defined supra, to nucleic acid sequences that encode an antibody of the invention.

The nucleic acid sequence may be obtained, and the nucleotide sequence of the nucleic acid sequence determined, by any method known in the art. A nucleic acid sequence encoding an HIV envelope-like polypeptides antibody may be generated from nucleic acid from a suitable source.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook, et al., 1990, Molecular Cloning, A Laboratory Manual, 2d Ed., Cold Spring Harbor Laboratory, Cold Spring Harbor, N.Y. and Ausubel, et al., eds., 1998, Current Protocols in Molecular Biology, John Wiley & Sons, NY, which are both incorporated by reference herein in their entireties), to generate antibodies having a different amino acid sequence, for example, to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia, et al., 1998, J Mol Biol 278: 457-479 for a listing of human framework regions). In a specific embodiment, one or more amino acid substitutions may be made within the framework regions, and in certain embodiments, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the nucleic acid sequence are encompassed by the present invention and within the skill of the art.

Recombinant expression of an antibody that binds to HIV envelope-like polypeptides requires construction of an expression vector containing a nucleic acid sequence that encodes the antibody. Once a nucleic acid sequence encoding an antibody molecule, heavy or light chain of an antibody, or fragment thereof (preferably, but not necessarily, containing the heavy or light chain variable domain) of the invention has been obtained, the vector for the production of the antibody molecule may be produced by recombinant DNA technology using techniques well-known in the art. Thus, methods for preparing an antibody by expressing a nucleic acid sequence encoding the antibody are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a fragment thereof, or a heavy or light chain CDR, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody may be cloned into such a vector for expression of the entire heavy chain, the entire light chain, or both the entire heavy and light chains.

The expression vector is transferred to a host cell by conventional techniques and the transfected cells are then cultured by conventional techniques to produce an antibody of the invention. Thus, the invention includes host cells containing a nucleic acid sequence encoding an antibody, or a heavy or light chain thereof, or fragment thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells that may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA, or cosmid DNA expression vectors containing antibody coding sequences; yeast (e.g., *Saccharomyces cerevisiae* or *Pichia pastoris*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecules, are used for the expression of a recombinant antibody molecule. For example, mammalian cells such as Chinese hamster ovary cells (CHO), in conjunction with a vector such as the major intermediate early gene promoter element from human cytomegalovirus, is an effective expression system for antibodies (Foecking, et al., 1986, Gene 45:101; and Cockett, et al., 1990, Bio/Technology 8:2).

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors that direct the expression of high levels of fusion protein products that are readily purified may be desirable. Such vectors include, but are not limited to, the *E. coli* expression vector pUR278 (Ruther, et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J Biol Chem 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of virus-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc Natl Acad Sci USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner, et al., 1987, Methods in Enzymol 153:51-544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, W138, BT483, Hs578T, HTB2, BT2O and T47D, NS0 (a murine myeloma cell line that does not endogenously produce any immunoglobulin chains), CRL7O3O, and HsS78Bst cells.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter, enhancer, sequences, transcription terminators, polyadenylation sites, etc.) and a selectable marker. Following the introduction of the foreign DNA, engineered cells may be allowed to grow for 1-2 days in an enriched media, and then are switched to selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the antibody molecule. Such engineered cell lines may be particularly useful in screening and evaluation of compositions that interact directly or indirectly with the antibody molecule.

A number of selection systems may be used; as non-limiting examples, the herpes simplex virus thymidine kinase (Wigler, et al., 1977, Cell 11:223), hypoxanthine-guanine phosphoribosyltransferase (Szybalska & Szybalski, 1992, Proc. Natl. Acad. Sci. USA 48:202), and adenine phosphoribosyltransferase (Lowy, et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler, et al., 1980, Proc Natl Acad Sci USA 77:357; O'Hare, et al., 1981, Proc Natl Acad Sci USA 78:1527); gpt, which confers resistance to mycophenolic acid (Mulligan & Berg, 1981, Proc Natl Acad Sci USA 78:2072); neo, which confers resistance to the aminoglycoside G-418 (Wu and Wu, 1991, Biotherapy 3:87-95; Tolstoshev, 1993, Ann Rev Pharmacol Toxicol 32:573-596; Mulligan, 1993, Science 260:926-932; and Morgan and Anderson, 1993, Ann Rev Biochem 62: 191-217; 1993, TIB TECH 11(5):155-2 15); and hygro, which confers resistance to hygromycin (Santerre, et al., 1984, Gene 30:147). Methods commonly known in the art of recombinant DNA technology may be routinely applied to select the desired recombinant clone, and such methods are described, for example, in Ausubel, et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds.), Current Protocols in Human Genetics, John Wiley & Sons, NY (1994); Colberre-Garapin, et al., 1981, J Mol Biol 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse, et al., 1983, Mol Cell Biol 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc Natl Acad Sci USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies may be fused to heterologous polypeptide sequences described herein or otherwise known in the art to facilitate purification.

Once a conjugate of the invention has been produced by recombinant expression or by chemical synthesis, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

Pharmaceutical Preparations

Vaccines

In one embodiment the antigens of the invention are present in pharmaceutical compositions/preparations. Generally they are in the form of a polypeptide which can be prepared by the various methods describe herein and known in the art. In some embodiments, the antigens are provided as polynucleotides encoding the antigen which are then transcribed and translated in vitro.

The HIV envelope-like polypeptides and the polynucleotides encoding them are useful, for example, as vaccine compositions. Compositions of the invention can be used as vaccine compositions, for example, to enhance or induce an immune response of a subject to HIV Immune responses which can be enhanced or induced include both humoral and cell-mediated responses. Compositions comprising particular preparations of HIV envelope-like molecules can be tested for the ability to induce an immune response using assays well known in the art. For example, a composition can be injected into a laboratory animal, such as a rat or mouse, and the animal can be monitored for the appearance of immune reactants, such as antibodies, directed against the HIV envelope-like polypeptides. Alternatively, assays such as cytotoxic T lymphocyte assays can be performed to determine whether a particular composition of HIV envelope-like molecule is immunogenic.

For use as a vaccine, a composition of the invention preferably comprises a HIV envelope-like polypeptide. Vaccine compositions of the invention typically comprise a physiologically compatible carrier. Physiologically compatible carriers are well known to those in the art and include diluents, adjuvants or excipients. Such carriers include, but are not limited to, a simple low salt solution which permits preservation of the integrity of the HIV envelope-like polypeptide, e.g., 10 mM NaCl, 0.1 mM EDTA, or to large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in HIV envelope-like polypeptides compositions, for example, mineral salts such as hydrochlorides, hydrobromides, phosphates, or sulfates, as well as salts of organic acids such as acetates, proprionates, malonates, or benzoates. Compositions of the invention can also contain liquids, such as water, saline, glycerol, and ethanol, as well as substances such as wetting agents, emulsifying agents, or pH buffering agents.

Various methods can be used to administer an HIV envelope-like molecule vaccine composition to a human, including intravenous, intramuscular, or subcutaneous injection. Vaccine compositions of the invention are administered at a dose effective to induce an immune response against the HIV envelope-like polypeptide. The particular dosages of the composition used to enhance an immune response will vary, for example, according to the HIV envelope-like compositions being used and the mammal to which the composition is administered. Generally, about 5 μg to about 50 μg of HIV envelope-like polypeptide per kg of patient body weight, about 50 μg to about 5 mg/kg, about 100 μg to about 500 μg/kg, or about 200 to about 250 μg/kg will be administered to an adult human. Such ranges by no means preclude use of a higher or lower amount of a component, as might be warranted in a particular application. For example, the actual dose and schedule may vary depending on whether the compositions are administered in combination with other pharmaceutical compositions, or depending on individual differences in pharmacokinetics, drug disposition, and metabolism.

The antigens and/or adjuvants of the invention can also be delivered using one or more gene vectors, administered via nucleic acid immunization or the like using standard gene delivery protocols. Methods for gene delivery are known in the art. See, e.g., U.S. Pat. Nos. 5,399,346, 5,580,859, 5,589,466. The constructs can be delivered either subcutaneously, epidermally, intradermally, intramuscularly, intravenous, mucosally (such as nasally, rectally and vaginally), intraperitoneally, orally or combinations thereof.

An exemplary replication-deficient gene delivery vehicle that may be used in the practice of the present invention is any of the alphavirus vectors, described in, for example, U.S. Pat. Nos. 6,342,372; 6,329,201 and International Publication WO 01/92552.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, BioTechniques (1989) 7:980-990; Miller, A. D., Human Gene Therapy (1990) 1:5-14; Scarpa et al., Virology (1991) 180:849-852; Burns et al., Proc. Natl. Acad. Sci. USA (1993) 90:8033-8037; and Boris-Lawrie and Temin, Cur. Opin. Genet. Develop. (1993) 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070

(published 23 Jan. 1992) and WO 93/03769 (published 4 Mar. 1993); Lebkowski et al., Molec. Cell. Biol. (1988) 8:3988-3996; Vincent et al. Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering polynucleotides, mucosally and otherwise, is the enterically administered recombinant poxvirus vaccines described by Small, Jr., P. A., et al. (U.S. Pat. No. 5,676,950, issued Oct. 14, 1997, herein incorporated by reference) as well as the vaccinia virus and avian poxviruses. By way of example, vaccinia virus recombinants expressing the genes can be constructed as follows. The DNA encoding the antigens and/or adjuvants of the invention is first inserted into an appropriate vector so that it is adjacent to a vaccinia promoter and flanking vaccinia DNA sequences, such as the sequence encoding thymidine kinase (TK). This vector is then used to transfect cells that are simultaneously infected with vaccinia. Homologous recombination serves to insert the vaccinia promoter plus the gene encoding the coding sequences of interest into the viral genome. The resulting TK recombinant can be selected by culturing the cells in the presence of 5-bromodeoxyuridine and picking viral plaques resistant thereto.

Alternatively, avipoxviruses, such as the fowlpox and canarypox viruses, can also be used to deliver genes encoding the antigens and/or adjuvants of the invention. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545. Picornavirus-derived vectors can also be used. (See, e.g., U.S. Pat. Nos. 5,614,413 and 6,063,384). Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

A vaccinia based infection/transfection system can be conveniently used to provide for inducible, transient expression of the coding sequences of interest (for example, sequences encoding the antigens or adjuvants of the invention) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase that in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135,855.

One or more additional HIV antigens can be used in the vaccine and methods of this invention. For instance, the HIV envelope-like polypeptides can be used with additional HIV antigens. The additional HIV antigens may be administered simultaneously, prior to or after administration of the HIV envelope-like polypeptides.

In addition, an immuno-modulatory factor may be added to the pharmaceutical composition. An "immuno-modulatory factor" refers to a molecule, for example a protein that is capable of modulating an immune response or DNA vectors encoding a given imuno-modulatory factor. Non-limiting examples of immunomodulatory factors include lymphokines (also known as cytokines), such as IL-6, TGF-beta, IL-1, IL-2, IL-3, IL-15, etc.); and chemokines (e.g., secreted proteins such as macrophage inhibiting factor). Certain cytokines, for example TRANCE, flt-3L, and a secreted form of CD40L are capable of enhancing the immunostimulatory capacity of APCs. Non-limiting examples of cytokines which may be used alone or in combination in the practice of the present invention include, interleukin-2 (IL-2), stem cell factor (SCF), interleukin 3 (IL-3), interleukin 6 (IL-6), interleukin 12 (IL-12), G-CSF, granulocyte macropliage-colony stimulating factor (GM-CSF), interleukin-1 alpha (IL-1.alpha.), interleukin-11 (IL-11), MIP-1-X.gamma.MIP-β, leukemia inhibitory factor (LIF), c-kit ligand, thrombopoietin (TPO), CD40 ligand (CD40L), tumor necrosis factor-related activation-induced cytokine (TRANCE) and flt3 ligand (flt-3L). Cytokines are commercially available from several vendors such as, for example, Genzyme (Framingham, Mass.), Amgen (Thousand Oaks, Calif.), R&D Systems and Immunex (Seattle, Wash.). The sequences of many of these molecules are also available, for example, from the GenBank database. It is intended, although not always explicitly stated, that molecules having similar biological activity as wild-type or purified cytokines (e.g., recombinantly produced or mutants thereof) and nucleic acid encoding these molecules are intended to be used within the spirit and scope of the invention.

The compositions of the invention will typically be formulated with pharmaceutically acceptable carriers or diluents. As used herein, the term "pharmaceutically acceptable carrier" refers to a carrier for administration of the antigens which does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee et al. (1997) J Microencapsul. 14(2):197-210; O'Hagan et al. (1993) Vaccine 1 (2):149-54. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from E. coli.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of acceptable excipients is available in the well-known Remington's Pharmaceutical Sciences.

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

Generally, the HIV envelope-like polypeptides will be operatively coupled to an immunocarrier. The vaccines of the invention additionally contemplate use of immunocarriers, such as ankyrin repeat domains, C3d, influenza virus, albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein-derived or non-protein derived substances are known to those skilled in the art.

Antibody Pharmaceutical Preparations

The present invention provides compositions comprising an antibody of the invention. In a further embodiment, the composition includes an antibody and a carrier. The invention provides a pharmaceutical composition comprising an effective amount of an antibody of the invention and a pharmaceutically acceptable carrier or vehicle. In a specific embodiment, a pharmaceutical composition comprises an effective amount of an antibody of the invention and a pharmaceutical acceptable carrier or vehicle. The pharmaceutical compositions are suitable for veterinary and/or human administration.

The pharmaceutical compositions of the present invention can be in any form that allows for the composition to be administered to a subject, said subject preferably being an animal, including, but not limited to a human, mammal, or non-human animal, such as a monkey, cow, horse, sheep, pig, fowl, cat, dog, mouse, rat, rabbit, guinea pig, etc., and is more preferably a mammal, and most preferably a human.

The antibody compositions of the invention can be in the form of a solid, liquid or gas (aerosol). Preferably the composition is in a liquid pharmaceutical composition. Typical routes of administration may include, without limitation, oral, topical, parenteral, sublingual, rectal, vaginal, ocular, intradermal, intratumoral, intracerebral, intrathecal, and intranasal. Parenteral administration includes subcutaneous injections, intravenous, intramuscular, intraperitoneal, intrapleural, intrasternal injection or infusion techniques. In a specific embodiment, the compositions are administered parenterally. In a more specific embodiment, the compositions are administered intravenously. Pharmaceutical compositions of the invention can be formulated so as to allow an antibody of the invention to be bioavailable upon administration of the composition to a subject. Compositions can take the form of one or more dosage units, where, for example, a tablet can be a single dosage unit, and a container of an antibody of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject is in need of treatment of, the use of the composition as part of a multi-drug regimen, the particular form of the antibody of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

Physiologically compatible carriers are well known to those in the art and include diluents, adjuvants or excipients. Such carriers include, but are not limited to, a simple low salt solution which permits preservation of the integrity of the HIV envelope-like polypeptide, e.g., 10 mM NaCl, 0.1 mM EDTA, or to large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in HIV envelope-like polypeptides compositions, for example, mineral salts such as hydrochlorides, hydrobromides, phosphates, or sulfates, as well as salts of organic acids such as acetates, proprionates, malonates, or benzoates. Compositions of the invention can also contain liquids, such as water, saline, glycerol, and ethanol, as well as substances such as wetting agents, emulsifying agents, or pH buffering agents. The antibody pharmaceutical composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The antibody liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as EDTA; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions comprise an effective amount of an antibody of the invention such that a suitable dosage will be obtained (see infra, for suitable dosages). Typically, this amount is at least 0.01% of an antibody of the invention by weight of the composition. When intended for oral administration, this amount can be varied to be between 0.1% and 80% by weight of the composition. Preferred oral compositions can comprise from between 4% and 50% of the antibody of the invention by weight of the composition. Preferred compositions of the present invention are prepared so that a parenteral dosage unit contains from between 0.01% and 2% by weight of the antibody of the invention.

The compositions of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering an antibody of the invention. In certain embodiments, more than one antibody of the invention is administered to a subject. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer, a cancerous tumor or a pre-cancerous condition).

In one embodiment, the antibodies or antibody conjugates of the invention are administered parenterally. In a specific embodiment, the antibodies or antibody conjugates of the invention are administered intravenously.

In yet another embodiment, the antibody or antibody conjugates of the invention can be delivered in a controlled release system. In one embodiment, a pump can be used (see Sefton, CRC Crit Ref Biomed Eng 1987, 14, 201; Buchwald, et al., Surgery 1980, 88: 507; Saudek, et al., N Engl J Med 1989, 321: 574). In another embodiment, polymeric materials can be used (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, J Macromol Sci Rev Macromol Chem 1983, 23, 61; see also Levy, et al., Science 1985, 228, 190; During, et al., Ann Neurol, 1989, 25, 351; Howard, et al., J Neurosurg, 1989, 71, 105). Other controlled-release systems discussed in the review by Langer (Science 1990, 249, 1527-1533) can be used.

In another embodiment, polymeric materials can be used to achieve controlled or sustained release of the antibodies or antibody conjugates of the invention (see, e.g., U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in *Remington's Pharmaceutical Sciences* by E. W. Martin.

Sustained or directed release compositions that can be formulated include, but are not limited to, antibodies or antibody conjugates of the invention protected with differentially degradable coatings, e.g., by microencapsulation, multiple coatings, etc. It is also possible to freeze-dry the compositions and use the lyophilizates obtained, for example, for the preparation of products for injection.

In a preferred embodiment, the antibodies or antibody conjugates of the invention are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetics such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where an antibody of the invention is to be administered by infusion, it can be dispensed, for example, with an infusion bottle containing sterile pharmaceutical grade water or saline. Where the antibody of the invention is administered by injection, an ampoule of sterile water for injection or saline can be provided so that the ingredients can be mixed prior to administration.

The pharmaceutical compositions of the invention can be intended for topical administration, in which case the carrier can be in the form of a solution, emulsion, ointment or gel base. The base, for example, can comprise one or more of the following: petrolatum, lanolin, polyethylene glycols, beeswax, mineral oil, diluents such as water and alcohol, and emulsifiers and stabilizers. Thickening agents can be present in a composition for topical administration. If intended for transdermal administration, the composition can be in the form of a transdermal patch or an iontophoresis device.

Topical formulations can comprise a concentration of a conjugate of the invention of from between 0.01% and 10% w/v (weight per unit volume of composition).

The compositions can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid, liquid or gaseous form, the compositions of the present invention can comprise an additional active agent selected from among those including, but not limited to, an additional therapeutic agent, an antiemetic agent, a hematopoietic colony stimulating factor, an adjuvant therapy, a vaccine or other immune stimulating agent, an antibody/antibody fragment-based agent, an anti-depressant and an analgesic agent. For instance in a particular embodiment, the pharmaceutical composition comprises a conjugate of the invention, an additional agent, and a pharmaceutically acceptable carrier or vehicle.

The pharmaceutical compositions can be prepared using methodology well known in the pharmaceutical art. For example, a composition intended to be administered by injection can be prepared by combining a conjugate of the invention with water so as to form a solution. A surfactant can be added to facilitate the formation of a homogeneous solution or suspension. Surfactants are complexes that can non-covalently interact with a conjugate of the invention so as to facilitate dissolution or homogeneous suspension of the conjugate of the invention in the aqueous delivery system.

In one embodiment, the pharmaceutical compositions of the present invention may comprise one or more other therapies.

Methods of Use

The invention is also directed to methods for inducing an immune response in a subject by administering a pharmaceutical composition having an immunologically effective dose of one or more HIV envelope-like polypeptides. Administration can occur before or after HIV infection. Generally, the HIV envelope-like polypeptide is 80% or more identical to an amino acid sequence of FIG. 1. Suitable HIV envelope-like polypeptides include both mimotope and wild-type HIV envelope polypeptides (gp160). In some embodiments, the HIV envelope-like polypeptide has an amino acid sequence which is 85%, 90%, 95%, 96%, 97%, 98%, 99% or more identical to an amino acid sequence depicted in FIG. 1. In a preferred embodiment, the subject is administered one or more envelope-like polypeptides having an amino acid sequence which is identical to an amino acid sequence depicted in FIG. 1. Peptides suitable for inducing a protective immune response include HIV envelope-like peptides having the amino acid sequence of SEQ ID NOs: 1-84, of these SEQ ID NOs: 21, 23, 25, 28, 29 and 31 correspond to HIV V3 envelope region SEQ ID NOs: 34, 35, 37, 38 and 39 correspond to the HIV envelope C-terminal region. Alternatively, the HIV envelope-like polypeptides included in the pharmaceutical composition may be wild-type HIV envelope proteins, for example, peptides that are 80% or more identical to SEQ ID NOs: 85-92. Preferably, the HIV envelope-like polypeptides are fusion polypeptide, e.g., mimotope-carrier fusion polypeptide. In some embodiments, the method of inducing an immune response includes the sequential or co-administration of a nucleic acid encoding a HIV envelope polypeptide (e.g., gp160).

Administering a therapeutically effective dose of an antibody that specifically binds to an HIV envelope-like polypeptide may also be used as a means for treating or preventing an HIV infection in a subject. Administration can occur before or after HIV infection. Generally, the HIV envelope like polypeptide has an amino acid sequence which is 80% or more identical to an amino acid sequence depicted in FIG. 1. Suitable antibodies bind to HIV envelope-like polypeptides include both mimotope and wild-type HIV envelope polypeptides (gp160). In some embodiments, the antibodies bind to HIV envelope-like polypeptides having an amino acid sequence which is 85%, 90%, 95%, 96%, 97%, 98%, 99% or more identical to an amino acid sequence depicted in FIG. 1. In a preferred embodiment, the antibody binds to an envelope-like polypeptide having an amino acid sequence which is identical to an amino acid sequence depicted in FIG. 1. In one embodiment, the antibody binds to a mimotope of an HIV envelope peptide such as those illustrated in SEQ ID NOs: 1-84. More specifically the antibody binds to a mimotope of the HIV V3 envelope region, wherein the mimotope has an amino acid sequence which is 80% or more identical to SEQ ID NOs: 21, 23, 25, 28, 29 and 31. In another embodiment, the antibody used in the method of treatment is a mimotope derived from the HIV C-terminal envelope region and has an amino acid sequence which is 80% or more identical to the amino acid sequence of SEQ ID NOs: 34, 35, 37, 38 and 39. The antibodies used in the method may also be specific for and bind to wild-type HIV envelope proteins, for example, peptides that are 80% or more identical to SEQ ID NOs: 85-92.

Some terms relating to the use of the antigens and/or antibodies of this invention are defined as follows.

As used herein, the term "inducing an immune response" to an antigen or composition is the development in a subject of a humoral and/or a cellular immune response to an antigen present in the composition of interest.

The terms "treat," and "treating," as used herein, shall mean decrease, suppress, attenuate, diminish, arrest, or stabilize the development or progression of HIV or the symptoms associated with HIV (e.g., AIDS) in an animal who is infected with the viral disorder. The treatment may be complete, e.g., the total absence of HIV in a subject. The treatment may also be partial, such that the occurrence of infected cells in a subject is less than that which would have occurred without the present invention. Treatment results in the stabilization, reduction or elimination of the infected cells, an increase in the survival of the patient or a decrease of the symptoms of the disease.

The terms "prevent," "preventing," and "prevention," as used herein, shall refer to a decrease in the occurrence of HIV or decrease in the risk of acquiring HIV or its associated symptoms in a subject (e.g., AIDS). The prevention may be complete, e.g., the total absence of disease or pathological cells in a subject. The prevention may also be partial, such that the occurrence of the disease or pathological cells in a subject is less than that which would have occurred without the present invention.

The term "inhibits" as used herein with reference to an HIV infection refers to a decrease in viral transmission, decrease in virus binding to a cellular target or decrease in disease. For example, the polypeptides of the present invention induce an antibody response which is used to inhibit viral transmission, syncytium formation and disease associated with the virus (e.g. AIDS). A compound of the invention can be screened by many assays, known in the art and described herein, to determine whether the compound inhibits the virus (e.g., infectivity, transmission, etc.). For example, an antibody of the invention can be assayed for its ability to inhibit viral infectivity by contacting a cell culture that is incubated with the virus with a test compound. The antibody is found to inhibit viral infectivity when viral infectivity is 90%, 80%, 75%, 70%, 60%, 50%, 40%, 30%, 20%, 10%, or 5% or less in the presence of the test antibody as compared to a suitable control (subjected to an unspecific control-antibody).

The term "inhibit transmission", as used herein, refers to the antibody's ability to inhibit viral infection of cells, via, for example, cell—cell fusion or cell-free virus infection. Such infection may involve membrane fusion, as occurs in the case of enveloped viruses, or some other fusion event involving a viral structure and a cellular structure.

The term "inhibiting syncytium formation", as used herein, refers to an antibody's ability to inhibit or reduce the level of membrane fusion events between two or more moieties relative to the level of membrane fusion which occurs between said moieties in the absence of the agent. The moieties may be, for example, cell membranes or viral structures, such as viral envelopes.

The terms "therapeutically effective amount," or "therapeutically effective dose" refers to that amount of an agent (e.g., polypeptide or antibody) to produce the intended pharmacological, therapeutic or preventive result. The pharmacologically effective amount results in the amelioration of one or more symptoms of a viral disorder, or prevents the advancement of a viral disease, or causes the regression of the disease or decreases viral transmission. For example, a therapeutically effective amount preferably refers to the amount of a therapeutic compound (e.g., antibody) that decreases the rate of transmission, decreases HIV viral load, or decreases the number of infected cells, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more. A therapeutically effective amount, with reference to HIV, also refers to the amount of a therapeutic agent (e.g., antibody) that increases $CD4^+$ cell counts, increases time to progression to AIDS, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more.

The compositions will include "immunologically effective amounts" of HIV envelope-like antigen i.e. amounts sufficient to raise a specific immune response or, more preferably, to treat, reduce, or prevent HIV infection. An immune response can be detected by looking for antibodies to the HIV envelope-like antigen used (e.g. IgG or IgA) in patient samples (e.g. in blood or serum, in mesenteric lymph nodes, in spleen, in gastric mucosa, and/or in feces). The precise effective amount for a given patient will depend upon the patient's age, size, health, the nature and extent of the condition, the precise composition selected for administration, the patient's taxonomic group, the capacity of the patient's immune system to synthesize antibodies, the degree of protection desired, the formulation of the vaccine, the treating physician's assessment of the medical situation, and other relevant factors. Thus, it is not useful to specify an exact effective amount in advance, but the amount will fall in a relatively broad range that can be determined through routine trials, and is within the judgment of the clinician. For purposes of the present invention, an effective dose will typically be from about 0.01 mg/kg to 50 mg/kg in the individual to which it is administered. Preferably, the immune response is an antibody response which is specific for an HIV envelope polypeptide and inhibits an HIV infection.

The antigens (e.g., HIV envelope-like polypeptide) of this invention are expected to be valuable as vaccine immunogens due to their enhanced immunogenicity, enhanced stability and half-life, and their ability to elicit effective neutralizing antibodies that are broadly cross-reactive against a spectrum of HIV isolates and do not react with self-antigens (unlike antibodies elicited by many known gp41-based antigens). Accordingly, an embodiment of this invention includes a method of vaccinating against HIV infections in a subject comprising administering to said subject a pharmaceutical composition containing an amount of an antigen of the invention that is effective in immunizing (at least partially) against HIV infection.

The determination of a therapeutically effective dose is well within the capability of those skilled in the art. A therapeutically effective dose refers to the amount of an antibody that may be used to effectively treat a disease (e.g., cancer) compared with the efficacy that is evident in the absence of the therapeutically effective dose.

The therapeutically effective dose may be estimated initially in animal models (e.g., rats, mice, rabbits, dogs, or pigs). The animal model may also be used to determine the appropriate concentration range and route of administration. Such information may then be used to determine useful doses and routes for administration in humans.

The antigens and/or antibodies of the present invention may be administered alone or in combination with one or more additional therapeutic agents. Combination therapy includes administration of a single pharmaceutical dosage formulation which contains an antibody of the present invention and one or more additional therapeutic agents, as well as administration of the antibody of the present invention and each additional therapeutic agent in its own separate pharmaceutical dosage formulation. For example, an antibody of the present invention and a therapeutic agent may be administered to the patient together in a single intravenous composition or each agent may be administered in separate intravenous formulations.

Where separate dosage formulations are used, the antibody of the present invention and one or more additional therapeutic agents may be administered at essentially the same time (e.g., concurrently) or at separately staggered times (e.g., sequentially). The order of administration of the agents is not limited.

For example, in one aspect, co-administration of an antibody or antibody fragment of the invention together with one or more anti-HIV agents to potentiate the effect of either the antibody or the anti-HIV agent(s) or both is contemplated for use in treating HIV infections. Examples of anti-HIV agents include, but are not limited to AGENERASE (ampreavir), APTIVUS (tipranavir), ATRIPLA, COMBIVIR, RETROVIR, EPIVIR, CRIXIVAN (indinavir), EMTRIVA (emtricitabine), EPZICOM, FORTOVASE (saquinavir), FUZEON (enfuvirtide), HIVID (ddc/zalcitabine), INTELENCE (Etravirine), ISENTRESS (raltegravir), INVIRASE (saquinavir), KAETRA (lopinavir), LEXIVA (Fosamprenavir), NORVIR (ritonavir), PREZISTA (darunavir), RESCRTIPTOR (delavirdine), RETROVIR (AZT), REYATAZ (atazanavir), SUSTIVA (efavirenz), TRIZIVIR, VIDEX (ddl/didanosine), VIRACEPT (nelfinavir), VIRAMUNE (nevirapine), VIREAD (tenofovir disoproxil fumarate), ZERIT (d4t/stavudine) and ZIAGEN (abacavir).

Therapeutic efficacy and toxicity (e.g., $ED_{50}$—the dose therapeutically effective in 50% of the population and $LD_{50}$—the dose lethal to 50% of the population) of an antibody may be determined by standard pharmaceutical procedures in cell cultures or experimental animals. The dose ratio of toxic to therapeutic effects is the therapeutic index, and it may be expressed as the ratio, $LD_{50}/ED_{50}$. The data obtained from animal studies may used in formulating a range of dosage for human use. The dosage contained in such compositions may be within a range of circulating concentrations that include the $ED_{50}$ with little or no toxicity. The dosage varies within this range depending upon the dosage form employed, sensitivity of the patient, and the route of administration.

The exact dosage may be determined by the practitioner, in light of factors related to the patient who requires treatment. Dosage and administration may be adjusted to provide sufficient levels of the antibody or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy.

Effective in vivo dosages of an antigen and/or antibody are in the range of about 5 µg to about 500 µg/kg of patient body weight. For administration of polynucleotides encoding the antibodies, effective in vivo dosages are in the range of about 100 ng to about 500 µg of DNA.

The antibodies of the invention may be used as therapeutics in the treatment of HIV infection and/or AIDS. In addition, the antibodies may be used as prophylactic measures in previously uninfected individuals after acute exposure to an HIV virus (e.g. post-exposure prophylaxis). Examples of such prophylactic use of the antibodies may include, but are not limited to, prevention of virus transmission from mother to infant and other settings where the likelihood of HIV transmission exists, such as, for example, sexual transmission or accidents in health care settings wherein workers are exposed to HIV-containing blood products.

Effective dosages of the compositions of the invention to be administered may be determined through procedures described herein and well known to those in the art which address such parameters as biological half-life, bioavailability, and toxicity.

Assaying for Anti-HIV Activity

Described herein, are methods for evaluating the ability of a compound, such as the antibodies of the invention, to inhibit HIV infectivity activity both in vitro and in vivo. Specifically, such assays are described below and in Examples 1 and 5. Additional assays for evaluating anti-vial activity are well known to those with ordinary skill in the art.

The antiviral activity exhibited by the antibodies of the invention may be measured, for example, by easily performed in vitro assays, such as those described herein and known by those of ordinary skill in the art, which can test the antibody's ability to inhibit syncytia formation, or their ability to inhibit infection by cell-free virus (Madani, N., et al., *Journal of Virology*, 2007. 81(2): p. 532-538; Si, Z. H., M. Cayabyab, and J. Sodroski, *Journal of Virology*, 2001. 75(9): p. 4208-4218; Si, Z. H., et al., *PNAS USA*, 2004. 101(14): p. 5036-5041).

Using these assays, such parameters as the relative antiviral activity of the antibodies exhibit against a given strain of virus and/or the strain specific inhibitory activity of the peptide can be determined.

Assays to test an antibody's antiviral capabilities are contemplated with the present invention. For example, a reverse transcriptase (RT) assay may be utilized to test the antibody's ability to inhibit infection of $CD4^+$ cells by cell-free HIV. Such an assay may comprise culturing an appropriate concentration (i.e., Tissue Culture Infectious Dose 50) of virus and $CD4^+$ cells in the presence of the antibody's to be tested. Culture conditions well known to those in the art are used. A range of antibody concentrations may be used, in addition to a control culture wherein no antibody has been added. After incubation for an appropriate period (e.g., 7 days) of culturing, a cell-free supernatant is prepared, using standard procedures, and tested for the present of RT activity as a measure of successful infection. The RT activity may be tested using standard techniques such as those described by, for example, Goff et al. (Goff, S. et al., 1981, *J. Virol.* 38:239-248) and/or Willey et al. (Willey, R. et al., 1988, *J. Virol.* 62:139-147). These references are incorporated herein by reference in their entirety.

In vivo assays may also be utilized to test, for example, the antiviral activity of the antibodies of the invention. To test for anti-HIV activity, for example, the in vivo model described in Barnett et al. (Barnett, S. W. et al., 1994, *Science* 266:642-646) may be used.

Additional assays for evaluating the effectiveness of the modified viral polypeptides are well known to those of ordinary skill in the art.

Kits

The present invention also encompasses a finished packaged and labeled pharmaceutical product. This article of manufacture includes the appropriate unit dosage form in an appropriate vessel or container such as a glass vial or other container that is hermetically sealed. The pharmaceutical product may contain, for example, a compound of the invention (e.g., HIV envelope-like polypeptide, antibody) in a unit dosage form in a first container, and in a second container, sterile water for injection. Alternatively, the unit dosage form may be a solid suitable for oral, transdermal, intranasal, intravaginal, cervical ring, or topical delivery.

In a specific embodiment, the unit dosage form is suitable for intravenous, intramuscular, intranasal, oral, intravaginal, cervical, topical or subcutaneous delivery. Thus, the invention encompasses solutions, solids, foams, gels, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures (e.g. detection and quantitation of infection), and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a compound of the invention, and wherein said packaging material includes instruction means which indicate that said compound can be used to prevent, manage, treat, and/or ameliorate one or more symptoms associated with a viral disease by administering specific doses and using specific dosing regimens as described herein.

The following examples are provided merely as illustrative of various aspects of the invention and shall not be construed to limit the invention in any way.

EXAMPLES

Example 1. Materials and Methods for Practicing Examples 2-7

Monkey Serum

Serum was collected from rhesus monkey RK1-8, an animal described earlier [Song R J, et al. (2006). J Virol 80: 8729-8738]. Briefly, this monkey was infected with a pathogenic R5 SHIV, termed SHIV-1157ip, which encodes the env gene of HIV-C, the most prevalent HIV-1 subtype worldwide. Approximately 10% of the rhesus monkeys infected with SHIV-1157ip or the related SHIV-1157ipd3N4 developed high-titer, broadly reactive nAbs not only against homologous SHIV-1157ip and the corresponding primary HIV-C, but also against heterologous strains of HIV-1 clades B and C (Table 1 paper [p. 42, Humbert et al., PLOS One submitted]).

Phage Display Biopanning.

Paramagnetic beads (Dynabeads M-280 tosyl activated; Invitrogen, Carlsbad Calif., USA) were coated with a rabbit anti-monkey IgG (Sigma-Aldrich, St. Louis Mo., USA) according to the manufacturer's instructions. Coated beads were pre-incubated while rotating for 2 h at room temperature with rhesus monkey serum (1:250 in phosphate buffered saline/0.25% gelatin, PBSG; Gibco-Invitrogen, Grand Island N.Y., USA; Fisher Scientific, Fair Lawn N.J., USA). Beads were washed 5× with PBSG/0.5% (w/v) Tween-20 (PBSGT; Sigma-Aldrich) and then incubated while rotating overnight at 4° C. with 10 µl of the original phage-displayed peptide library (New England Biolabs, Ipswich Mass., USA). Biopannings of all three libraries (7mer, cyclic 7mer and 12mer) were performed in parallel using separate tubes. The next day, beads were washed 10× with 1 ml PBSGT and bound phages were eluted by pH shift with 0.2 M glycine-HCl pH 2.2 supplemented with 1 mg/ml BSA (Sigma-Aldrich). After neutralization with 1 M Tris-HCl pH 9.1 (Sigma-Aldrich), eluted phages were subjected to negative selection using pooled sera from non-infected control monkeys. Phages remaining from the negative selections were amplified in Escherichia coli (ER2738, New England Biolabs), precipitated overnight at 4° C. (20% PEG-8000/2.5 M NaCl; Fisher Scientific) and used for a second and third round of selection. After the third positive selection, the phages were titered, and single clones were picked and tested by phage ELISA for specific binding. Positives clones were amplified and sequenced to deduce their peptide insert.

Phage ELISA.

Plates (Greiner-Bio-One GmbH, Frickenhausen, Germany) were coated overnight at 4° C. with 100 µl/well serum (1:5,000 in carbonate-bicarbonate buffer; Sigma-Aldrich). The next day, plates were blocked (1 h, room temperature) with 200 µl/well 3% casein (Sigma-Aldrich) in PBS/0.5% Tween-20 (PBSCT) and washed 3× with 300 µl dH$_2$O in an automated plate washer (BioTek Instruments, Inc., Winooski Vt., USA). Then, 70 µl of control or positively selected phages that had been amplified overnight were added to 30 µl PBSCT and incubated overnight at 4° C. Plates were washed 3× and incubated for 1 h at RT with 100 µl/well of an anti-phage HRP-conjugated antibody (1:2,000 in PBSCT; GE Healthcare Bio-Sciences Corp., Piscataway N.J., USA). After washing 5×, the plates were developed with 100 µl/well o-phenylenediamine in phosphate-citrate buffer (Sigma-Aldrich), stopped with 100 µl/well 1 N H$_2$SO$_4$ (VWR, West Chester Pa., USA) and read at 490/620 nm.

Mimotope Analysis.

Figure 2:
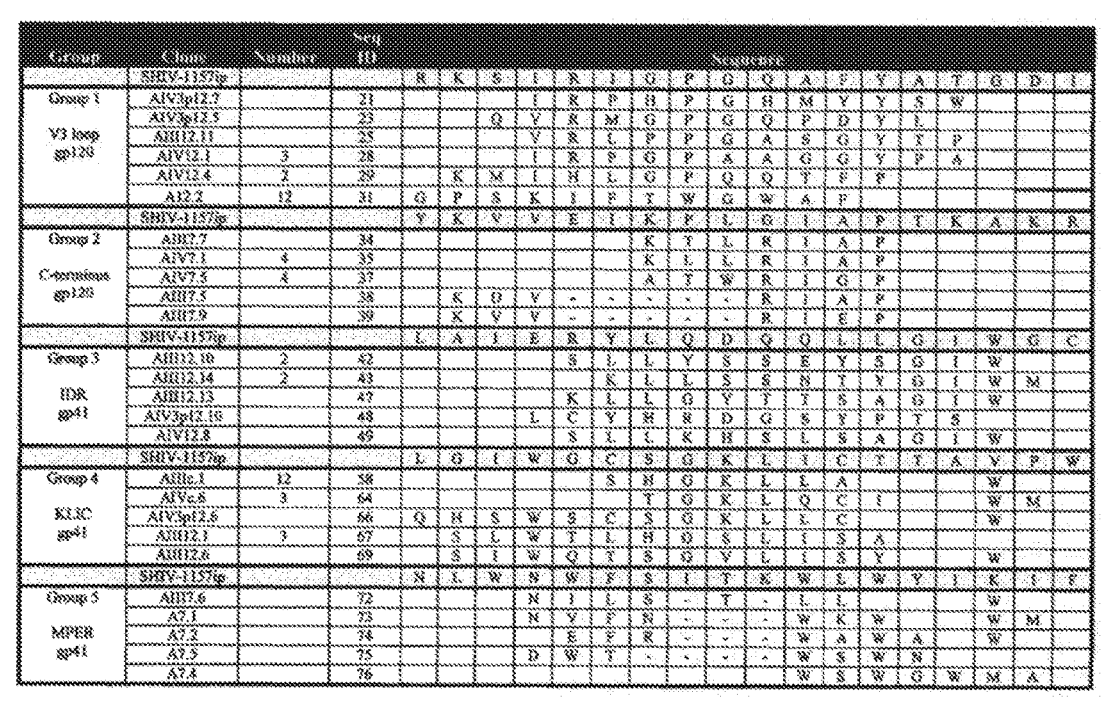

Phage insert sequences were analyzed using the computer program 3DEX [Schreiber A, et al. (2005). J Comput Chem 26: 879-887]. After checking for linear homology to SHIV-1157ip gp160 [Song R J, et al. (2006). J Virol 80: 8729-8738], the peptide sequences were compared to published PDB structure files of HIV-1 gp120 [Kwong P D, et al. (2000). Structure 8: 1329-1339, Huang C C, et al. (2005). Science 310: 1025-1028] to identify conformational homology. Phages were grouped according to their peptide motifs, and selected phages were used for further analysis and immunization studies (FIG. 2).

Immunization of Mice.

Figure 7:
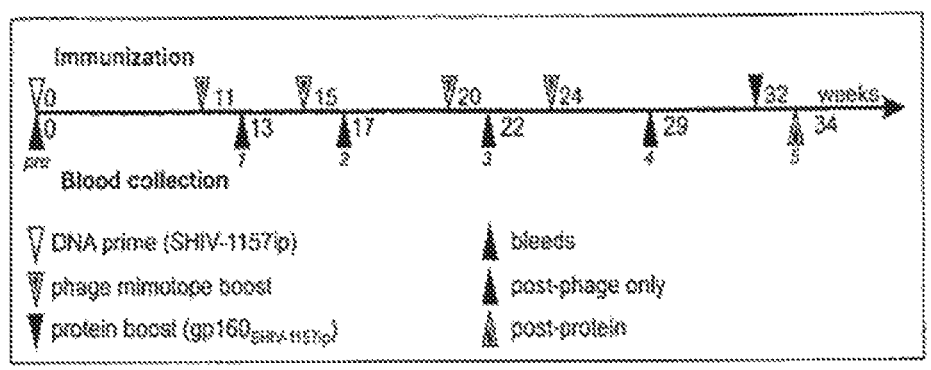
FIG. 7 illustrates the immunizations and blood collection schedule for the mouse study of Example 5.

Selected recombinant phages were grouped according to motifs; each group consisted of 5-6 phages with similar but not identical peptide sequences. Phages of each group were combined and used as five different mixtures for immunization. Mice were primed once with SHIV-1157ip env DNA (intramuscularly; 100 µg in 100 µl PBS) and boosted subcutaneously (s.c.) with $10^{12}$ phage particles in 100 µl PBS/MPL (Sigma-Aldrich) every 4-5 weeks. Serum samples were collected 2-5 weeks after each boost. After four phage boosts, serum samples were tested for their neutralizing capacity against HIV-1$_{SF162.LS}$ and SHIV-1157ip. In a pilot study, 11 mice were given an additional boost with trimeric SHIV-1157ip gp160 (s.c.; 20 µg in 100 µl PBS with incomplete Freund's adjuvant (IFA) (Sigma-Aldrich) and their sera were tested for the presence of neutralizing antibodies (FIG. 7).

Neutralization Assay.

SHIV-1175ip was prepared in rhesus monkey PBMC, HIV pIndieC was prepared in human PBMC and HIV$_{SF162.LS}$ pseudovirus was prepared using cotransfection of 293T cells with an env expression plasmid and Δenv backbone vector. TZM-b1 cells encode the luciferase gene under the control of the HIV-1 promoter; both CD4 and CCR5 are also expressed on the cell surface (AIDS Research and Reference Program, Division of AIDS, NIAID, NIH). A total of 5000 cells/well were seeded overnight in 100 µl DMEM/10% FCS (Gibco-Invitrogen, Grand Island N.Y., USA). Serial 2-fold dilutions of immune sera were prepared in triplicates in 96-well round-bottom plates (Becton Dickenson, Franklin Lakes N.J., USA). In parallel, the pre-immune sera were serially diluted and used as controls. "Virus only" wells received 50 µl medium. The virus was diluted (1:500 for SHIV-1157ip: 36 ng/ml p27; 1:500 for HIV pIndieC: 35 ng/ml p24; 1:300 for HIV$_{SF162.LS}$: 300 ng/ml p24) and 50 µl of virus was added to all wells. The plate was incubated for 1 h at 37° C. in 5% CO$_2$, after which time 10 µl of a 400 µg/ml DEAE-Dextran solution (Sigma-Aldrich) was added to all wells and the entire mixture was transferred into the 96-well flat-bottom plate with the seeded TZM-b1 cells. The next day, medium was replaced with fresh medium and incubated another 24 h. Bright-Glo luciferase substrate (Promega, Madison Wis., USA) was added to the plate the following day and luciferase activity was measured. The percent neutralization was calculated using the following equation:

$$\% \text{ Neutralization} = \left[1 - \left(\frac{\text{Luciferase immune serum}}{\text{Luciferase pre-immune serum}}\right)\right] * 100$$

Dot Spot Analysis.

Trimeric SHIV-1157 gp160 was spotted onto a nitrocellulose membrane (Whatman GmbH, Dassel, Germany) (50 ng/spot in native or reduced conditions (10 mM TCEP (Pierce, Rockford Ill., USA); 1% SDS (Sigma-Aldrich); boiled for 2 min) Strips were blocked with PBSCT for 1 h at room temperature and incubated overnight at 4° C. with antibodies (diluted in PBSCT). The next day, strips were washed 3× with PBST and incubated with anti-monkey IgG horse-radish peroxidase (HRP)-conjugate (1:2,000 in PBSCT; Sigma-Aldrich). After 1 h at room temperature, strips were washed 5× with PBST and developed using Opti-4CN substrate (Bio-Rad Laboratories, Hercules Calif., USA) (FIG. 5).

ELISA.

Plates were coated overnight at 4° C. with 100 ng/well native or reduced (10 mM TCEP/1% SDS; boiled for 2 min) proteins in 100 µl coating buffer. After washing 3×, plates were blocked with 200 µl/well PBSCT for 1 h at room temperature and then incubated overnight at 4° C. with mouse serum (1:175) or rhesus monkey serum (1:800; 100 µl/well diluted in PBSCT). Plates were washed 3× and incubated with horse-radish peroxidase (HRP)-conjugated antibodies (1:2,000 in PBSCT, 100 µl/well) for 1 h at room temperature. After washing 5×, plates were developed using 100 µl/well o-phenylenediamine in phosphate-citrate buffer, stopped with 100 µl/well 1 N $H_2SO_4$ and read at 490/620 nm.

Mimotope Fusion Proteins.

Fusion proteins were cloned into the expression vector pPEPTIDE according to manufacturer's instructions (Mo-BiTec GmbH, Göttingen, Germany). Briefly, phage peptide insert were amplified using two primers (pPeptide-rev: 5'-GGCCCGG GGATCCTAACTTTCAACAGTTTCGGCCGAACCTCCACG; (SEQ ID NO.: 94) pPeptide-fw: 5'-CGCCCGCGG ATTAATGGCCCTTTAGTGGTACCTTTCTATTCTCACTCT (SEQ ID NO.: 95) to introduce the underlined cloning restriction sites, digested with AseI and BamHI (Fermentas Inc., Glen Burnie Md., USA) and gel-purified using Nucleo-Spin Extract II (Macherey-Nagel Inc., Bethlehem Pa., USA). Six ng of mimotope DNA were ligated with 100 ng vector and transformed into BL21(DE3) cells (Novagen, Madison Wis., USA). After sequence analysis, proteins were expressed according to the manual and purified using standard chromatography using the Ni-charged Profinity IMAC resin (Bio-Rad). Of note, the vector encodes a His tag to assess fusion protein expression. The plasmid is based on the pET expression vector system and induction of the T7 promoter leads to the expression of a highly expressed fusion protein (89 aa) followed by a higher affinity poly(His) region (53 aa) for purification and the C-terminal mimotope. The expressed mimotope fusion protein migrates at a size of around 26 kD.

Western Blot.

Figure 6:
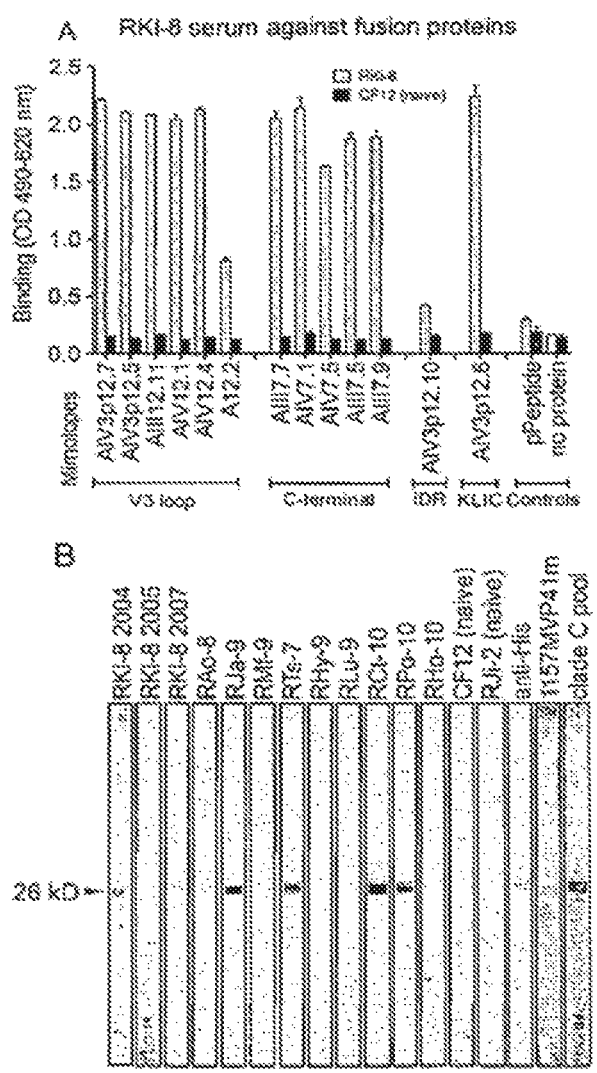
FIG. 6 illustrates the reactivity profile of mimotope fusion proteins by ELISA and Western Blot. (A) Mimotope fusion proteins were tested by ELISA with sera from monkeys RKl-8 and CF12. (B) Cross-reactivity of mimotope fusion protein AIV12.4 (26 kD; arrowhead) with a panel of rhesus monkey sera by Western blot.

Standard SDS PAGE was performed with 40 µg protein per gel (Bio-Rad). Protein was transferred onto a nitrocellulose membrane (Bio-Rad) using a wet blot apparatus (Bio-Rad). The membrane was cut into strips, blocked with 3% PBSCT and individual strips were incubated with the appropriate serum (1:200) or antibodies (1:1,000 in 3% PBSCT) overnight at 4° C. Membranes were washed 3× and incubated for 1 h at room temperature with an HRP-conjugated antibody (1:2,000 in 3% PBSCT). After washing 5×, the strips were developed with Opti-4CN substrate (Bio-Rad) (FIG. 6).

Statistical Analysis.

Statistics were calculated using a two-tailed paired t test and only applied to matching pairs of mice comparing the significance between the post-phage boosts and post-gp160 boost (GraphPad Prism 5 for Windows, GraphPad Software).

Example 2. Selection of HIV-C Env-Specific Mimotopes

Polyclonal IgG was isolated from a rhesus monkey infected with SHIV-1157ip, an R5 SHIV strain encoding env of a recently transmitted Zambian HIV-C. This monkey (animal RKl-8) had developed high-titer, broadly reactive neutralizing antibodies (nAbs) that neutralized primary strains of HIV-1 clades B and C (FIG. 2). Serum IgG was immobilized on paramagnetic beads used to screening three different phage-displayed random peptide libraries (7mer, cyclic 7mer, 12mer). For each screening, 94 single clones were tested in phage ELISA for their specificity using SHIV-positive and SHIV-negative serum in parallel. Positive clones were amplified and sequenced. Peptide insert sequences were grouped according to their motifs and analyzed for linear homology to parental $gp160_{SHIV-1157ip}$. 78 different clones were obtained; 9 clones represented mimotopes of the V2 loop of gp120, 21 clones represented mimotopes of the V3 loop of gp120 and 8 clones represented mimotopes of the C-terminal domain of gp120. The remainder thirty-four clones resembled regions on gp41 (the majority of the clones represented a subdomain of the immunodominant region (IDR), which is referred to as the immunodominant loop [Zolla-Pazner S (2004). Nat Rev Immunol 4: 199-210] and contains the KLIC motif (20 clones); seven clones shared homology with IDR outside the immunodominant loop as well as several amino acid residues of the N-terminal heptad repeat. Seven other clones showed homology to the MPER. Six phage inserts exhibited no apparent linear similarity to $gp160_{SHIV-1157ip}$.

Figure 3:
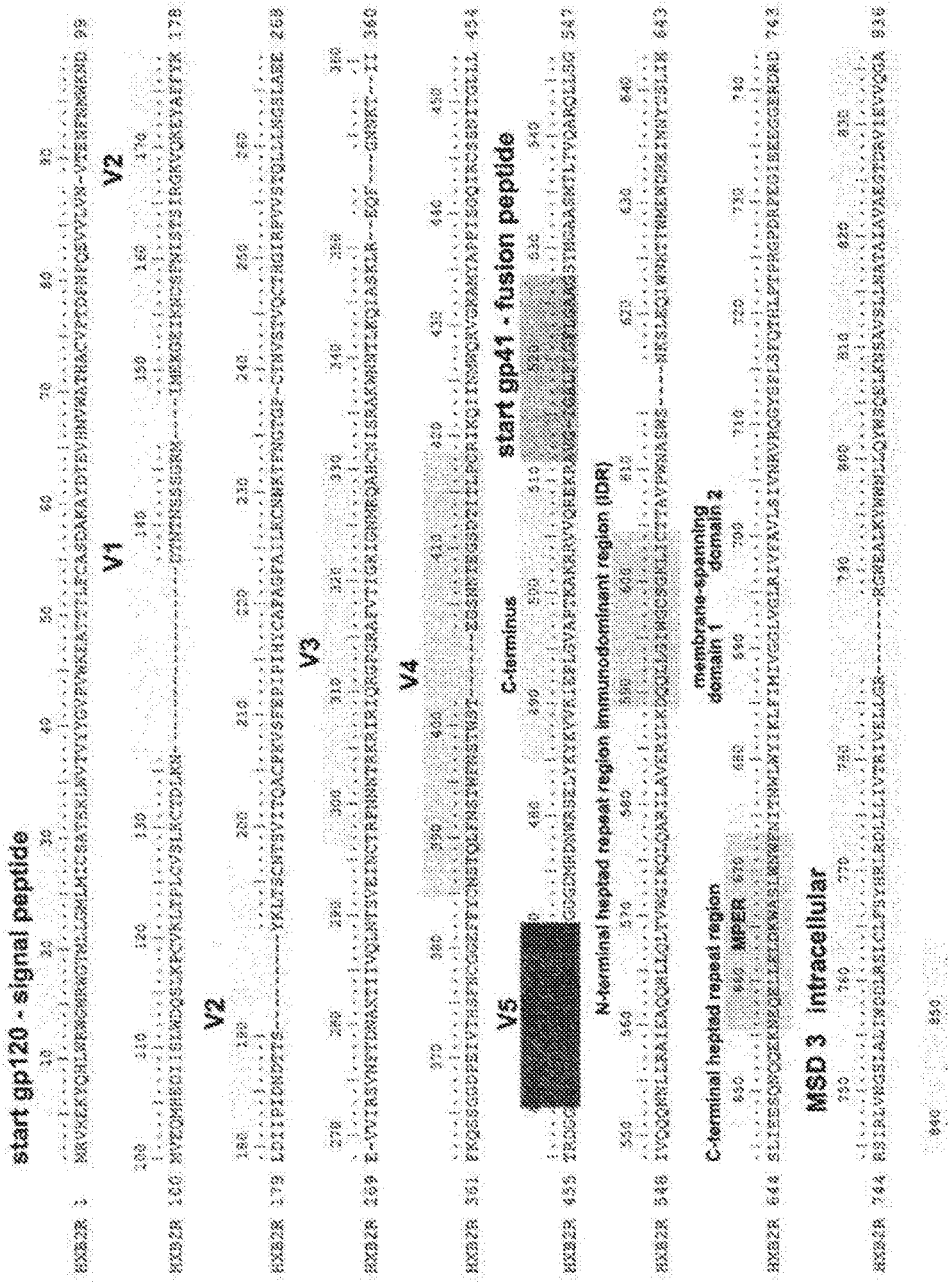
Figure 4:
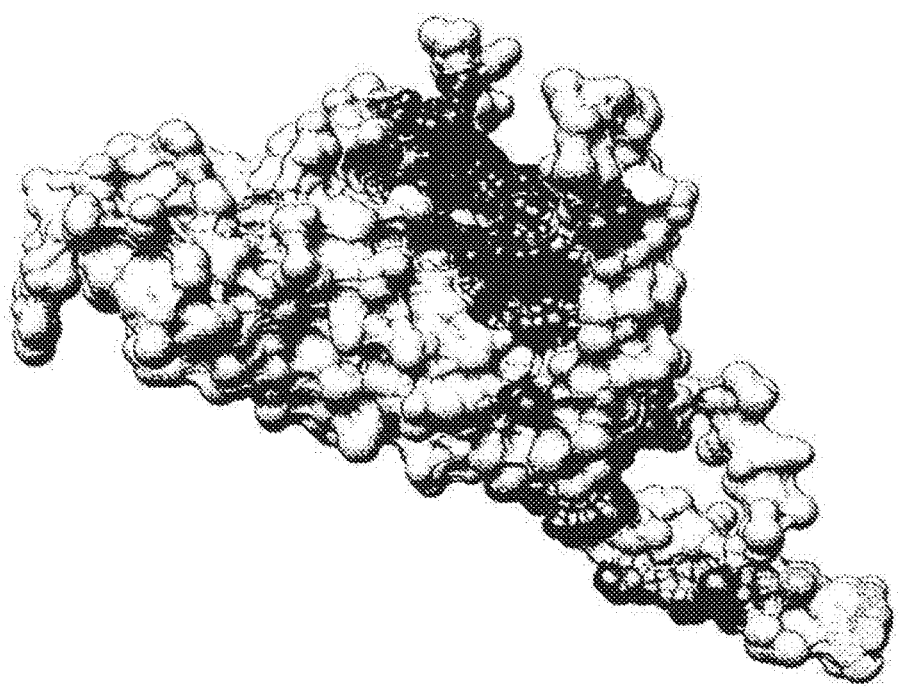

Since several mimotopes displayed only minimal linear homology to $gp160_{SHIV-1157ip}$, these were believed to exhibit predominantly conformational homology. Using 3DEX software and a published gp120 structure conformational mimotopes were identified. This approach identified a V3 mimotope which combines linear with structural homology (FIG. 2, clone A12.2; FIG. 4). We compared the primary envelope sequence of the structure file (PDB-ID: 2B4C; HIV-1 subtype B strain JR-FL) and SHIV-1157ip. The amino acids in that stretch of V3 are almost identical in sequence (inset FIG. 4). 3DEX found two motifs: one that comprises four amino acids at the crown of the V3 loop (FIG. 4, yellow/ orange); and a second one that consists of another four amino acids located near the crown (FIG. 4, green). Even though these eight amino acids are discontinuous, they are found in neighboring locations at the Env surface.

Example 3. Identification of a Conformational Mimotope of HIV-C Env

To confirm that antibody binding to mimotope A12.2 involves interaction with a conformational epitope and thus depends on the structural integrity of the target HIV-C gp160, antibody binding, under native and reduced conditions to the region on HIV-1 Env represented by the mimotope was assessed. Antibodies from the polyclonal rhesus monkey serum were first isolated by affinity purification with immobilized recombinant phage. The phage-affinity-purified antibodies were then subjected to a dot spot analysis with homologous, trimeric $gp160_{SHIV-1157ip}$ immobilized under native and denaturing conditions (FIG. 5).

Binding of antibodies specific for clone A12.2 was abolished when trimeric gp160 was denatured (FIG. 5, field A1 and B1), although specific binding was demonstrated to native Env. As control a control antibodies specific for a phage clone with greater linear homology to the V3 loop (AIV12.4) were used. As expected, these antibodies recognized the native as well as the denatured forms of gp160 (FIG. 5, field A2 and B2). The control without spotted gp160 (FIG. 5, row C) showed no nonspecific antibody binding on any strips. An additional positive control involved spotting anti-monkey IgG (FIG. 5, row D) and confirmed that equal amounts of phage-affinity-purified antibodies had been applied to all strips.

Example 4. Reactivity Profile of Mimotopes in the Context of Fusion Proteins

To analyze if the HIV-1 Env mimotope motif groups represent common antibody epitopes found in sera with broadly reactive nAbs, selected mimotopes of all groups (except MPER) were cloned into fusion proteins and tested the latter by ELISA and Western blot analysis using a panel of rhesus monkey sera with broadly neutralizing activity against different HIV-1 clades. All monkeys show broadly reactive nAbs against the homologous SHIV-1157ip as well as against a heterologous HIV-1 clade C (pIndieC) and clade B ($HIV_{SF162LS}$). In addition to screening with serum from monkey RKl-8, sera from monkeys RAo-8, RJa-9 and RMf-9 were used for individual phage display selections. The analysis revealed similar motif patterns to RKl-8, including mimotopes representing immunodominant regions such as V3 and KLIC, but also identified new motifs representing stretches of the Kennedy peptide in gp41 and as yet unidentified regions.

To assess if the mimotopes in the context of a fusion protein have conserved their structure, ELISAs was performed with sera from RKl-8. All mimotope fusion proteins were recognized by serum antibodies of RKl-8 (FIG. 6A). Of note, there is also binding to the conformational mimotope A12.2. Individual serum samples from 11 rhesus monkeys that included nine other monkeys with broadly reactive nAbs and two naïve animals displayed cross-reactivity of the KLIC mimotope with most of the sera from the monkey cohort with high-level nAbs. Notably, several rhesus monkey sera recognized selected V3 mimics, especially the two mimotopes AIV3p12.5 and AIV12.4. Motifs isolated with serum from monkey RKl-8 representing the conserved C-terminus of gp120 and the IDR did not react with sera from our rhesus monkey panel, although reactivity was seen with autologous serum. Two naïve control sera did not detect the fusion proteins and a control fusion protein (pPeptide; empty backbone of fusion protein without mimotope insert) was not detected by any of the rhesus monkey sera.

To confirm the ELISA results, all rhesus monkey sera were tested for specific binding to the fusion proteins by Western blots. RKl-8 and other monkey sera from various time points detected the AIV12.4 mimotope. The naïve control sera CF12 and RJi-2 did not bind to the mimotope fusion protein; whereas the positive anti-His antibody control detected the fusion protein migrating at a MW of 26 kD. Further parental serum from the HIV 1157i-infected human (1157MVP41m) and a serum pool of HIV-C-infected individuals; both recognized the mimotope (FIG. 6B).

Thus, the ELISA and Western blot results show that the mimotopes expressed in the context of a fusion protein conserved their structure and were recognized by the monkey serum from which they were selected as well as by other sera from our cohort.

Example 5. Immunization Studies in Mice

To assess if the mimotopes representing different regions of HIV Env are immunogenic, vaccine studies in mice were performed. Only single priming with a DNA vector encoding the entire gp160, which will not generate binding or nAb responses was sued. We reasoned that a single DNA priming would imprint the immune system with the correct image of native gp160 structures, without diverting antibody responses to immunodominant but ultimately unimportant Env regions. Instead, we hypothesized that our boosting with mimotopes would allow us to manipulate humoral immune responses by focusing them on important structural domains.

Specifically, first a DNA inoculation was used to prime the immune system with the entire HIV-1 Env. This was followed by phage boosting to focus the antibody response to a certain area of gp160.

Recombinant phages were grouped according to their peptide motifs and were combined into five mixtures to immunize mice (FIG. 2). First, all mice received one priming immunization with a DNA vector encoding $gp160_{SHIV-1157ip}$; this single DNA inoculation was previously shown to be insufficient for induction of binding antibodies or nAbs. All mice were then boosted four times with phage particles (intervals of 4-5 weeks) and their immune sera were assessed for binding abs and nAbs (FIG. 7).

Antibody binding titers for each group was measured for binding to $gp160_{SHIV-1157ip}$ by ELISA after the four phage boosts. Mean titers ranged from 1:125 to 1:1362, and almost all mice developed anti-Env titers. The lowest titer was observed the MPER group, the highest in the C-terminal domain.

Post-phage boost sera (4$^{th}$ bleed) were tested for neutralization of a heterologous HIV-1 clade B strain, $HIV_{SF162LS}$; 59% of the animals had measurable, cross-clade anti-HIV-1 nAbs. The mean $IC_{50}$ in all groups ranged from 1:19 to 1:70. Surprisingly, four out of the six mice immunized with mimotopes representing the C-terminal domain had nAbs, including two animals with $IC_{50}$ values>1:100. To our knowledge, this is the first report of the C-terminus of gp120 being linked to the induction of nAb responses.

To examine whether DNA prime/recombinant phage boosts had induced maximal nAb responses or if a boost with native, multimeric gp160 would be beneficial, 11 mice were boosted (6 from the V3, 1 from the C-terminal, 2 from each, the IDR and KLIC group) with $gp160_{SHIV-1157ip}$ and compared with the immune sera from those obtained after phage-boosts only. Mean Env-ELISA titers were 1:1,220 after four phage boosts compared to 1:2,748 after the additional gp160 boost, an increase that did not reach statistical significance. When tested for nAb responses against homologous SHIV-1157ip or heterologous $HIV-1_{SF162LS}$, the additional Env boost did not significantly raise nAb titers against either virus (p=0.8544 and p=0.3935, respectively; Data not shown, Humbert et al. PLOS One Manuscript (Submitted)), implying that maximal responses had been induced by DNA prime/phage boosting. Thus, the higher ELISA antibody titer after protein boosting did not translate into better nAb titers.

Example 6. Analysis of Vaccination-Induced Antibodies

The ability of antibodies induced by the different immunogens to react with native versus denatured HIV-1 gp160 was determined. It is possible that the mixture of similar but not identical mimotopes is able to broaden the immune response and to induce antibodies against conformational epitopes rather than linear ones. The V3 mimotopes show incomplete linear homology to gp160 and contains structure-specific homologies. In contrast, the gp120 C-terminal mimotopes are primarily linear.

The post-protein boost sera were tested (5th bleed) for reactivity against native and reduced HIV-1 gp160 by ELISA (FIG. 8). Sera from two mice boosted with V3-loop mimotopes showed decreased binding upon denaturation of Env (7-14-fold). In contrast, the signal obtained with serum from the mouse boosted with mimotopes representing the HIV-1 gp120 C-terminus decreased only 1.7-fold. These data imply that the V3-loop mimotopes induced conformational antibody responses, whereas the gp120 C-terminal mimotopes induced predominantly linear antibody responses.

Mimotope-induced antibodies against the gp41 IDR (FIG. 8; mouse #3.2) showed slightly increased binding upon denaturation of gp160$_{SHIV-1157ip}$; whereas serum antibodies from mouse #4.2 immunized with the potentially conformational KLIC motifs exhibited decreased binding after target denaturation (FIG. 8), implying that they are specific for conformational epitopes.

Example 7. Hybridoma Production

A mouse immunized with V3 loop mimotopes (SEQ ID NOs: 21, 23, 25, 28, 29 and 31) was used to generate monoclonal antibodies (mAbs). 14 positive wells were identified and four were picked for a subcloning procedure. All four clones were shown to be monoclonal and producing IgG1 (19-40 µg/ml medium). These four clones were designated Group 1 in FIG. 2.

IgG1-positive supernatants from all four monoclonal hybridomas were tested for their ability to bind to HIV Env preparations made from different strains. Specific binding was observed not only to Env from the homologous virus, but also to Env from HIV$_{1084i}$ (clade C), HIV$_{Bal}$ (clade B), and HIV$_{SF162}$ (clade B). Therefore, the IgG1 secreted by the monoclonal mouse hybridomas recognize HIV Env domains that are conserved across different clades.

Supernatants with defined antibody concentrations were tested for their ability to neutralize HIV$_{SF162.LS}$. Two out of the three supernatants were able to neutralize the virus (IC$_{50}$ levels: ~10 µg/ml).

Also, mAb generation from one mouse immunized with C-terminal mimotopes was initiated. 13 positive were identified and four subcloned. All clones bind various Env proteins from different strains (as described above). Neutralization assays against the clade B virus SF162.LS showed neutralizing activity for these clones (not knowing the secreted antibody concentration in the medium).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

We claim:

1. An isolated HIV envelope-like polypeptide, wherein said polypeptide comprises a mimotope of a HIV envelope C-terminal region and an amino acid sequence of SEQ ID: 35.

2. The isolated HIV envelope-like polypeptide of claim 1, wherein said polypeptide is a fusion polypeptide.

3. A composition comprising the HIV envelope-like polypeptide of claim 1 and a pharmacologically acceptable carrier.

4. A kit comprising the composition of claim 3 and instructions for use.

5. The isolated HIV envelope-like polypeptide of claim 2, wherein the fusion polypeptide contains a histidine tag.

6. The isolated HIV envelope-like polypeptide of claim 2, wherein the fusion polypeptide contains glutathione S-transferase.

7. The isolated HIV envelope-like polypeptide of claim 2, wherein the fusion polypeptide contains an immuno-carrier polypeptide.

8. The composition of claim 3, wherein said polypeptide is a fusion polypeptide.

9. The composition of claim 8, wherein the fusion polypeptide contains a histidine tag.

10. The composition of claim 8, wherein the fusion polypeptide contains glutathione S-transferase.

11. The composition of claim 8, wherein the fusion polypeptide contains an immuno-carrier polypeptide.

12. The kit of claim 4, wherein said composition contains a fusion polypeptide.

13. The kit of claim 12, wherein the fusion polypeptide contains a histidine tag.

14. The kit of claim 12, wherein the fusion polypeptide contains glutathione S-transferase.

15. The kit of claim 12, wherein the fusion polypeptide contains an immuno-carrier polypeptide.

16. An isolated nucleic acid encoding the isolated HIV envelope-like polypeptide of claim 1.

* * * * *

SEQUENCE LISTING

```
<160> NUMBER OF SEQ ID NOS: 114

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Gln Ile Arg Asp Lys Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Leu Ile Arg Asp Lys Gln
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Gln Val Arg Asp Lys Gln
```

```
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Leu Val Arg Asp Lys Gln
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ala Ile Arg Asp Lys Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Ala Ile Arg Asp Lys Gln
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Met Ile Arg Asp Lys Met
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr His Arg Glu Gln Pro Ser
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 9

Thr Ser Val Lys His Arg Leu
1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Met Pro Leu Pro Lys Pro Ile Arg Thr Gly Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ile Gln Phe Pro Lys Pro Ile Arg Leu Gly Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Thr Pro Gln Lys Val Leu Arg Leu Gly Pro Phe
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ser His Trp Thr Thr Lys Gly Arg Leu Val Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Thr Arg Arg Met Gly Pro
1               5

<210> SEQ ID NO 15

<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Glu Ile Arg Leu Gly Pro
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Tyr Ile His Leu Gly Pro
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Arg Thr Gly Pro Gly Val
1               5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 18

Thr Ile Lys Thr Ile Arg Thr Glu Xaa Arg Asn Xaa
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Thr Trp Arg Ile Gly Pro
1               5

<210> SEQ ID NO 20
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

His Arg Pro Gly Pro Gly Ala His His Tyr Leu Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Arg Pro His Pro Gly His Met Tyr Tyr Ser Trp
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Arg Phe Gly Pro Gly Met Pro Phe Tyr His
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Val Arg Met Gly Pro Gly Gln Pro Asp Tyr Leu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Arg Pro Pro Pro Gly Gln Pro His Phe Thr Phe
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Arg Leu Pro Pro Gly Ala Ser Gly Tyr Thr Pro
```

```
1               5                   10
```

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Val Arg Leu Pro Pro Gly Ala Ser Gly Tyr Thr Pro
1               5                   10
```

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 27

```
Ala Leu Xaa Pro Gly Pro Gly Ser Pro Leu Phe Thr
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Ile Arg Pro Gly Pro Ala Ala Gly Gly Tyr Pro Ala
1               5                   10
```

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Lys Met Ile His Leu Gly Pro Gln Gln Thr Phe Pro
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Lys Met Ile His Leu Gly Pro Gln Gln Thr Phe Pro
1               5                   10
```

<210> SEQ ID NO 31
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Pro Ser Lys Ile Phe Thr Trp Gly Trp Ala Phe
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Thr Phe Thr Trp Ser Trp
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Leu Ile Arg Val Ala Pro
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Thr Leu Arg Ile Ala Pro
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Leu Leu Arg Ile Ala Pro
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Ile Ile Arg Thr Ala Pro
```

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Thr Trp Arg Ile Gly Pro
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Asp Val Arg Ile Ala Pro
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Val Val Arg Ile Glu Pro
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Val Val Arg Thr Ala Pro
1               5

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Leu Leu Val Pro Ser Glu Thr Arg Gly Ile Trp
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Ser Leu Leu Tyr Ser Ser Glu Tyr Ser Gly Ile Trp
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Leu Leu Ser Ser Asn Thr Tyr Gly Ile Trp Met
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Leu Leu Ser Ser Asn Thr Tyr Gly Ile Trp Met
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Leu Leu Ser Ser Asn Thr Tyr Gly Ile Trp Met
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Leu Leu Cys Ser Ala Pro Thr Gln Leu Trp Cys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Leu Leu Gly Tyr Thr Thr Ser Ala Gly Ile Trp
1               5                   10

<210> SEQ ID NO 48

```
<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Cys Tyr His Arg Asp Gly Ser Tyr Pro Thr Ser
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Leu Leu Lys His Ser Leu Ser Ala Gly Ile Trp
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Leu Leu Lys His Ser Leu Ser Ala Gly Ile Trp
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Pro Gly Leu Ser Lys Leu
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Gly Lys Leu Pro Asn Leu
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53
```

```
Gln Gly Lys Leu Leu Pro Ala
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Gly Lys Leu Leu Pro Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Lys Leu Pro Glu Leu
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 56

Xaa Gly Lys Ile Pro Glu Leu
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Tyr Gly Lys Leu Ser Leu Phe
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser His Gly Lys Leu Leu Ala
1               5

<210> SEQ ID NO 59
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Tyr Gly Lys Leu Leu Ala
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Gly Lys Leu Leu Pro Glu
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Leu Gly Lys Leu Val Gly
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gly Lys Met Leu Pro Ala
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Cys Gly Lys Leu Val Cys
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64
```

```
Thr Gly Lys Leu Gln Cys Ile
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Phe Gly Lys Leu Leu Ala
1               5

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln His Ser Trp Ser Cys Ser Gly Lys Leu Leu Cys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Leu Trp Thr Leu His Gly Ser Leu Ile Ser Ala
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Leu Trp Thr Leu His Gly Ser Leu Ile Ser Ala
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Ile Trp Gln Thr Ser Gly Val Leu Ile Ser Tyr
1               5                   10

<210> SEQ ID NO 70
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 70

Gly Ile Trp Asn His Pro Ser Phe Leu Val Trp Glu
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid

<400> SEQUENCE: 71

Ser His Trp Ser Pro Xaa Arg Ser Xaa Arg Xaa Xaa
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asn Ile Leu Ser Thr Leu Leu
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asn Val Phe Asn Trp Lys Trp
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Glu Phe Arg Trp Ala Trp Ala
1               5

<210> SEQ ID NO 75
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Trp Thr Trp Ser Trp Asn
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Trp Ser Trp Gly Trp Met Ala
1               5

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Leu Trp Thr Leu His Gly Ser Leu Ile Ser Ala
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Ile Trp Gln Thr Ser Gly Val Leu Ile Ser Tyr
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Val Pro Pro Ser Phe Leu Ala Arg Trp Pro
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Ser Val Lys His Gly Leu
```

```
<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asn Pro Val Lys His Gly Leu
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Val Cys Thr His Arg Glu Cys
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Leu Cys Thr His Arg Glu Cys
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Lys Leu Trp Met Leu His
1               5

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Phe Asn Val Thr Thr Gly Ile Arg Asp Lys Lys Gln Lys Val Asn Ala
1               5                   10                  15

Leu Phe

<210> SEQ ID NO 86
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 86

Pro Asn Asn Asn Thr Arg Lys Ser Ile Arg Ile Gly Pro Gly Gln Ala
1               5                   10                  15

Phe Tyr

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Lys Ser Ile Arg Ile Gly Pro Gly Gln Ala Phe Tyr Ala Thr Gly
1               5                   10                  15

Asp Ile

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Lys Val Val Glu Ile Lys Pro Leu Gly Ile Ala Pro Thr Lys Ala
1               5                   10                  15

Lys Arg

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Ala Ile Glu Arg Tyr Leu Gln Asp Gln Gln Leu Leu Gly Ile Trp
1               5                   10                  15

Gly Cys

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Gly Ile Trp Gly Cys Ser Gly Lys Leu Ile Cys Thr Thr Ala Val
1               5                   10                  15

Pro Trp

<210> SEQ ID NO 91
<211> LENGTH: 18
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 91

```
Asn Glu Lys Asp Leu Leu Ala Leu Asp Ser Trp Glu Asn Leu Trp Asn
1               5                   10                  15
Trp Phe
```

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

```
Asn Leu Trp Asn Trp Phe Ser Ile Thr Lys Trp Leu Trp Tyr Ile Lys
1               5                   10                  15
Ile Phe
```

<210> SEQ ID NO 93
<211> LENGTH: 856
<212> TYPE: PRT
<213> ORGANISM: Human immunodeficiency virus

<400> SEQUENCE: 93

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
        50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
        130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
                180                 185                 190

Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
        210                 215                 220

Ile Leu Lys Cys Asn Asn Lys Thr Phe Asn Gly Thr Gly Pro Cys Thr
```

```
            225                 230                 235                 240
Asn Val Ser Thr Val Gln Cys Thr His Gly Ile Arg Pro Val Val Ser
            245                 250                 255
Thr Gln Leu Leu Leu Asn Gly Ser Leu Ala Glu Glu Val Val Ile
            260                 265                 270
Arg Ser Val Asn Phe Thr Asp Asn Ala Lys Thr Ile Ile Val Gln Leu
            275                 280                 285
Asn Thr Ser Val Glu Ile Asn Cys Thr Arg Pro Asn Asn Asn Thr Arg
            290                 295                 300
Lys Arg Ile Arg Ile Gln Arg Gly Pro Gly Arg Ala Phe Val Thr Ile
305                 310                 315                 320
Gly Lys Ile Gly Asn Met Arg Gln Ala His Cys Asn Ile Ser Arg Ala
            325                 330                 335
Lys Trp Asn Asn Thr Leu Lys Gln Ile Ala Ser Lys Leu Arg Glu Gln
            340                 345                 350
Phe Gly Asn Asn Lys Thr Ile Ile Phe Lys Gln Ser Ser Gly Gly Asp
            355                 360                 365
Pro Glu Ile Val Thr His Ser Phe Asn Cys Gly Gly Glu Phe Phe Tyr
            370                 375                 380
Cys Asn Ser Thr Gln Leu Phe Asn Ser Thr Trp Phe Asn Ser Thr Trp
385                 390                 395                 400
Ser Thr Glu Gly Ser Asn Asn Thr Glu Gly Ser Asp Thr Ile Thr Leu
            405                 410                 415
Pro Cys Arg Ile Lys Gln Ile Ile Asn Met Trp Gln Lys Val Gly Lys
            420                 425                 430
Ala Met Tyr Ala Pro Pro Ile Ser Gly Gln Ile Arg Cys Ser Ser Asn
            435                 440                 445
Ile Thr Gly Leu Leu Leu Thr Arg Asp Gly Gly Asn Ser Asn Asn Glu
            450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
            485                 490                 495
Ala Pro Thr Lys Ala Lys Arg Arg Val Val Gln Arg Glu Lys Arg Ala
            500                 505                 510
Val Gly Ile Gly Ala Leu Phe Leu Gly Phe Leu Gly Ala Ala Gly Ser
            515                 520                 525
Thr Met Gly Ala Ala Ser Met Thr Leu Thr Val Gln Ala Arg Gln Leu
            530                 535                 540
Leu Ser Gly Ile Val Gln Gln Asn Asn Leu Leu Arg Ala Ile Glu
545                 550                 555                 560
Ala Gln Gln His Leu Leu Gln Leu Thr Val Trp Gly Ile Lys Gln Leu
            565                 570                 575
Gln Ala Arg Ile Leu Ala Val Glu Arg Tyr Leu Lys Asp Gln Gln Leu
            580                 585                 590
Leu Gly Ile Trp Gly Cys Ser Gly Lys Leu Ile Cys Thr Thr Ala Val
            595                 600                 605
Pro Trp Asn Ala Ser Trp Ser Asn Lys Ser Leu Glu Gln Ile Trp Asn
            610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
            645                 650                 655
```

```
Glu Gln Glu Leu Leu Glu Leu Asp Lys Trp Ala Ser Leu Trp Asn Trp
            660                 665                 670
Phe Asn Ile Thr Asn Trp Leu Trp Tyr Ile Lys Leu Phe Ile Met Ile
        675                 680                 685
Val Gly Gly Leu Val Gly Leu Arg Ile Val Phe Ala Val Leu Ser Ile
    690                 695                 700
Val Asn Arg Val Arg Gln Gly Tyr Ser Pro Leu Ser Phe Gln Thr His
705                 710                 715                 720
Leu Pro Thr Pro Arg Gly Pro Asp Arg Pro Glu Gly Ile Glu Glu Glu
                725                 730                 735
Gly Gly Glu Arg Asp Arg Asp Arg Ser Ile Arg Leu Val Asn Gly Ser
            740                 745                 750
Leu Ala Leu Ile Trp Asp Asp Leu Arg Ser Leu Cys Leu Phe Ser Tyr
        755                 760                 765
His Arg Leu Arg Asp Leu Leu Leu Ile Val Thr Arg Ile Val Glu Leu
    770                 775                 780
Leu Gly Arg Arg Gly Trp Glu Ala Leu Lys Tyr Trp Trp Asn Leu Leu
785                 790                 795                 800
Gln Tyr Trp Ser Gln Glu Leu Lys Asn Ser Ala Val Ser Leu Leu Asn
                805                 810                 815
Ala Thr Ala Ile Ala Val Ala Glu Gly Thr Asp Arg Val Ile Glu Val
            820                 825                 830
Val Gln Gly Ala Cys Arg Ala Ile Arg His Ile Pro Arg Arg Ile Arg
        835                 840                 845
Gln Gly Leu Glu Arg Ile Leu Leu
    850                 855

<210> SEQ ID NO 94
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggcccgggga tcctaacttt caacagtttc ggccgaacct ccacc             45

<210> SEQ ID NO 95
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgcccgcgga ttaatggccc tttagtggta cctttctatt ctcactct         48

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Arg Lys Ser Ile Arg Ile
1               5
```

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Pro Gly Gln Ala Phe Tyr Ala
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Thr Arg Lys Ser Ile His Ile
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Pro Gly Arg Ala Phe Tyr Thr
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Pro Ser Lys Ile Phe
1               5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Trp Gly Trp Ala Phe
1               5

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 102

Thr Lys Trp Val His Thr Gly Pro Gly Glu Arg His
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Arg Pro Pro Pro Gly Trp Thr Ala Tyr Val Thr
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Met His Lys Pro Ile Arg Thr Gly Pro Ala Glu Val
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Met Ser Pro Pro Lys His Ile Arg Leu Gly Pro Asn
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Leu Arg Pro Gly Arg Ala Gln Pro Phe Tyr Ala
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Met Pro Arg Ala Ser Pro Gly Ser Pro His Tyr Thr
1               5                   10

<210> SEQ ID NO 108
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Leu Arg Pro Gly Met Ala Gln Pro Phe Tyr Ala
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

His Ala Lys Leu Ile Arg Thr Gly Pro Val Ala Val
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Thr Ser Arg Trp Asp Asp Val Arg His Ser Ile Thr
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Ala Ile Arg Ile Ala Pro
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Ala Ile Arg Val Gly Pro
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Lys Pro Leu Arg Leu Gly Pro
```

```
<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Arg Leu Gly Pro Gly Gln
1               5
```